(12) United States Patent
Besson

(10) Patent No.: US 7,352,887 B2
(45) Date of Patent: Apr. 1, 2008

(54) SCATTER REJECTION FOR COMPOSITE MEDICAL IMAGING SYSTEMS

(75) Inventor: Guy M. Besson, Broomfield, CO (US)

(73) Assignee: Hologic, Inc., Bedford, MA (US)

( * ) Notice: Subject to any disclaimer, the term of this patent is extended or adjusted under 35 U.S.C. 154(b) by 906 days.

(21) Appl. No.: 10/412,751

(22) Filed: Apr. 11, 2003

(65) Prior Publication Data

US 2004/0202360 A1    Oct. 14, 2004

(51) Int. Cl.
*G06K 9/00* (2006.01)
*A61B 6/00* (2006.01)

(52) U.S. Cl. ............................... 382/132; 378/7
(58) Field of Classification Search ........ 382/128–133; 378/7, 16, 19
See application file for complete search history.

(56) References Cited

U.S. PATENT DOCUMENTS

| | | | | |
|---|---|---|---|---|
| 4,149,081 A | * | 4/1979 | Seppi | 378/5 |
| 4,468,697 A | | 8/1984 | Verhoeven | 358/111 |
| 4,549,307 A | | 10/1985 | Macovski | 378/145 |
| 4,918,713 A | | 4/1990 | Honda | 378/99 |
| 5,081,581 A | | 1/1992 | Koral et al. | 364/413.24 |
| 5,434,414 A | | 7/1995 | Berlad et al. | 350/363.07 |
| 5,438,202 A | | 8/1995 | Matanzon et al. | 250/363.07 |
| 5,530,248 A | | 6/1996 | Natanzon et al. | 250/363.07 |
| 5,533,088 A | | 7/1996 | Fivez | 378/98.4 |
| 5,615,279 A | * | 3/1997 | Yoshioka et al. | 382/131 |
| 5,633,499 A | | 5/1997 | Lim et al. | 250/363.07 |
| 5,771,269 A | | 6/1998 | Chao | 378/5 |
| 6,018,565 A | | 1/2000 | Ergun et al. | 378/95 |
| 6,104,777 A | * | 8/2000 | Darboux et al. | 378/62 |
| 6,134,297 A | | 10/2000 | Chao | 378/98.12 |
| 6,298,109 B1 | | 10/2001 | Ergun et al. | 378/4 |
| 6,345,194 B1 | | 2/2002 | Nelson et al. | 600/425 |
| 6,639,964 B2 | * | 10/2003 | Schneider et al. | 378/7 |
| 7,092,482 B2 | * | 8/2006 | Besson | 378/37 |
| 2004/0202279 A1 | | 10/2004 | Besson et al. | |

* cited by examiner

*Primary Examiner*—Brian Werner
*Assistant Examiner*—Hadi Akhavannik
(74) *Attorney, Agent, or Firm*—Cooper & Dunham, LLP

(57) ABSTRACT

Scatter effects are reduced in a radiographic imaging device, such as a digital slot scan mammographic imaging device, by reducing detected scatter and processing detector information to compensate for scatter effects. In one embodiment, a digital mammographic imaging system (10) includes a source (24) for transmitting a narrow beam (28) and a detector assembly (32) for detecting the beam (28). The beam (28) and the detector assembly (32) are synchronously scanned across the patient's breast (48) to obtain an image. Collimator slats (74) are provided at the leading and trailing edges of the detector to reduce detected scatter. Additionally, attenuators (76 and 92) are provided at the ends of the scanned motion and at the anterior edge of the detector array to assist in determining a spatial intensity profile. The spatial intensity profile information together with other imaging signal and patient dependent parameters are used in image processing to estimate and compensate for various scatter effects including single and multiple scatters and Compton and Rayleigh scatter.

83 Claims, 14 Drawing Sheets

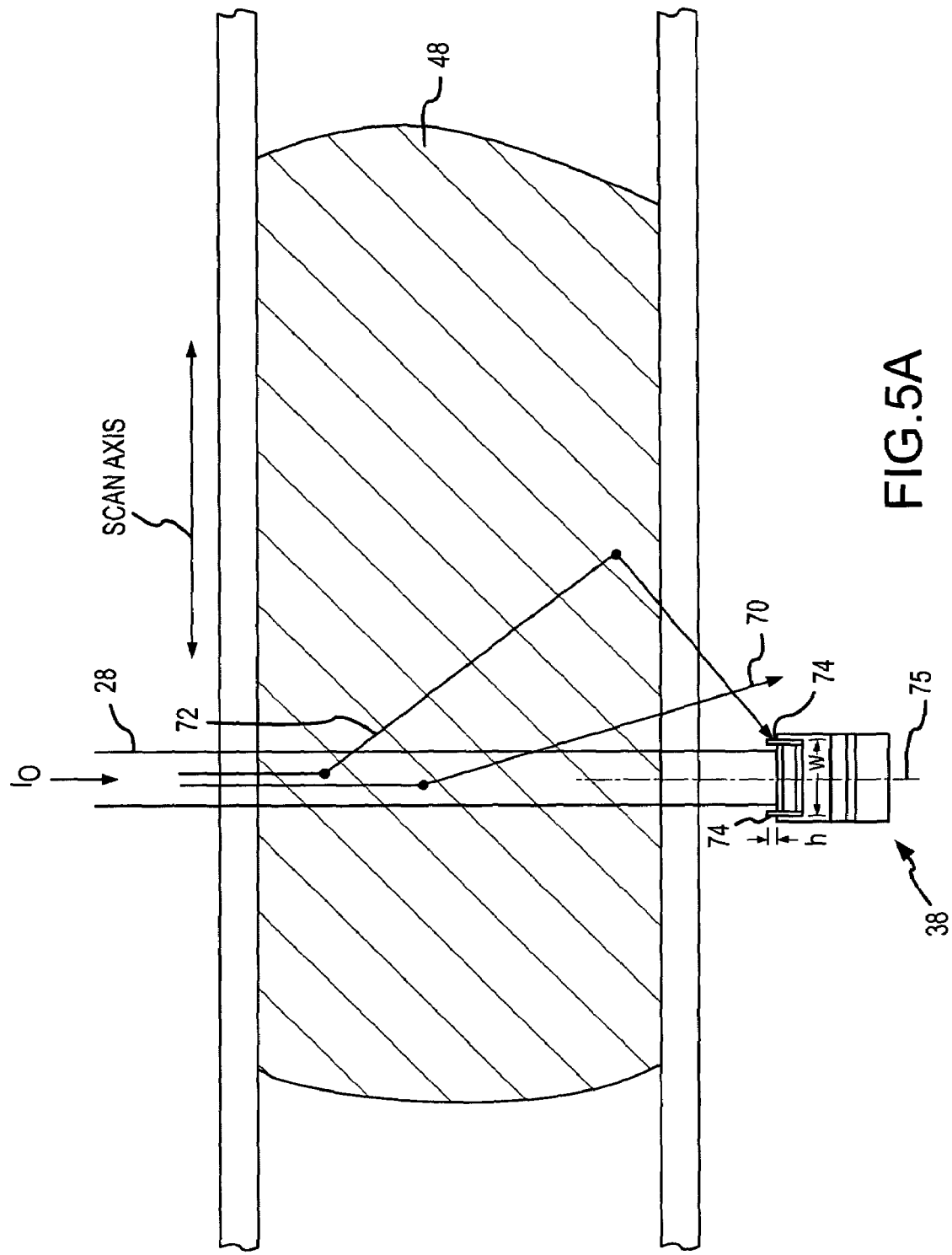

US 7,352,887 B2

SCATTER REJECTION FOR COMPOSITE MEDICAL IMAGING SYSTEMS

FIELD OF THE INVENTION

The present invention generally relates to medical imaging systems, and more particularly, to a method and system for enhancing radiographic images by removing or otherwise reducing the effects of scatter.

BACKGROUND OF THE INVENTION

Medical imaging is considered to be one of the most demanding applications of radiographic imaging, at least in terms of resolution and/or contrast. For instance, in the case of mammography it is generally desirable that a given imaging system be capable of obtaining images with a resolution on the order of fifty microns or better. Contrast requirements are also quite demanding since potential lesions and/or suspicious masses may exhibit x-ray attenuation characteristics similar to that of surrounding "healthy" tissue. With early detection of these lesions and/or masses being extremely desirable, enhancement of image resolution and/or contrast continues to be of increasing importance.

Mammography has been performed using both film-based and digital systems. In film-based systems, x-rays signals are generally transmitted through mammary tissue and received at an appropriate screen (e.g., phosphor screen). Light emitted from the screen, due to excitation by the impinging x-rays, is used to expose a light sensitive film. The film is then developed to yield an image of the patient's breast which can be viewed on a light box. By contrast, a full field light-sensitive detector may be utilized in place of the film in digital systems. In this context, "full field" indicates that the field imaged corresponds to the dimensions of the detector, although this may be substantially less than a full image area of interest to a physician, such as a full breast in the case of mammography. This detector outputs an electronic signal that is indicative of the received radiation intensity across a pixel region. In turn, the signal may be connected and processed into a viewable digital image (e.g., on a high-resolution monitor). As may be appreciated, digital image systems are becoming the norm in view of the attendant image storage and processing advantages.

Regardless of the mammography system utilized, granularity and screen noise may tend limit and/or distort the resultant image. For instance, the image contrast has been shown to be significantly affected by scattered radiation. Indeed, as a radiation source transmits a beam towards a tissue, the beam is both attenuated and scattered by the tissue. The scattered radiation that impinges on the detector (e.g. in the case of a digital system) from a path outside a "direct" or substantially straight path from the radiation source to the detector ("primary ray") is generally undesirable. Accordingly, mammographic images would ideally be generated "scatter-free".

One type of scatter is Compton scattering, also referred to as incoherent scattering, that typically occurs when an incident x-ray photon ejects an electron from an atom (e.g., a tissular atom), and an x-ray photon of lower energy is "scattered" from the atom. It may be said that relativistic energy and momentum are conserved during Compton scattering and that the scattered x-ray photon generally has less energy and therefore greater wavelength than the original incident photon. By contrast, Rayleigh scattering, also referred to as Thomson or coherent/classical scattering is generally characterized by an x-ray photon interacting with a whole atom so that the photon is scattered with substantially no change in internal energy to the scattering atom, nor to the x-ray photon. In other words, the wavelength of the scattered photon is generally similar to that of the incident photon prior to being scattered.

Various attempts have been made at reducing the incidence of scatter in radiographic imaging. For instance, the use of anti-scatter grids in full field digital imaging as described above has been shown to reduce the amount of scatter displayed in a resultant image. However, use of these grids generally coincides with a need for significant increase in tissue radiation dosages to generate images of desired resolution, signal-to-noise ratio and/or contrast. As another example, various opaque shields have been utilized to enable collection and calculation of an estimated scatter portion of the total beam intensity. However, use of these opaque shields has resulted in portions of the image information being lost (un-exposed, white areas on film). As a way of avoiding these lost areas in the resultant images, one or more subsequent images may be taken without the shields in an additional exposure period(s), and the scatter calculations of the first image can then be applied to the subsequent image(s). However, this obviously requires additional exposure of the patient to radiation doses, and means or process to remove the opaque shields between exposures.

SUMMARY OF THE INVENTION

The present invention is directed to a radiographic imaging device and associated methodology for reducing effects related to scattered radiation or scatter. In this regard, the invention reduces display artifact associated with scatter, resulting in improved contrast (for given imaging parameters) associated with features being imaged, for example, physiological features such as lesions, masses, calcifications and the like in the case of mammography. Such scatter effects are reduced according to the present invention by reducing detected scatter ("scatter rejection") and/or processing of detector information to compensate for scatter effects potentially present in such information ("scatter compensation"). This imaging improvement may allow for various advantages including reduced patient dosages, improved resolution and/or improved detection of low contrast features.

Various aspects of the invention may be advantageously implemented in connection with a composite imaging system that obtains imaging information for different portions of an area of interest at different times and aggregates this imaging information to generate composite imaging information for the area of interest. One example of such a composite imaging system is a slot scanner such as a digital slot scanner. Indeed, such slot scanners provide inherent advantages related to scatter rejection. Slot scanners utilize an imaging beam, such as a fan-shaped beam, that is narrower (in at least one dimension) than the area of interest to be imaged. To image the full area of interest, the narrow beam is scanned across the area of interest over an exposure time period. In the case of digital slot scanners, a composite image of the full area of interest may be constructed from the imaging information incrementally obtained during the exposure period.

In slot scanners, a narrow active detector area, e.g., closely corresponding to the cross-section of the imaging beam at the detector, is preferably moved in concert with the scanning motion of the imaging beam. In the case of digital detectors, this may be accomplished, for example, by physically moving a narrow array of detector elements or by electronically moving the active portion of a stationary full field array in concert with the scanning motion. In any such case, significant scatter rejection is achieved because radiation outside of the plane (or, more precisely, narrow wedge) including the signal source and the active detector area is not recorded as part of the image-forming information. It should be noted that pixels outside the area illuminated by the primary beam, may be used according to the present invention to directly record scatter-only information; such information may then be used to contribute (for example via interpolation) to the estimate of the scatter in the area adjacent that illuminated by the primary beam.

However, it has been recognized that scattered radiation, including single scatter radiation (associated with a single scatter event/interaction) and multiple scatter radiation (associated with more than one scatter event/interaction), associated with Rayleigh and/or Compton scattering, may still impinge on the active detector area, presenting a possibility of scatter related image degradation. The present invention reduces such potential degradation through enhanced scatter rejection and/or scatter compensation.

In accordance with one aspect of the present invention, a method and apparatus ("utility") is provided for rejecting scatter in the context of a composite imaging system. In particular, the utility involves operating a source to transmit a photonic imaging signal, such as an x-ray beam, to an area of interest of a patient's body such as a patient's breast for mammographic procedures. A detector detects at least portions of the imaging signal from the patient's body and provides an output reflecting imaging information for portions of the area of interest obtained at corresponding different times of an exposure period. A processor processes the detector output to provide composite imaging information for the area of interest. The utility further involves selectively blocking, on a spatially dependent basis, photons that are directed to a detector location by allowing passage of photons substantially on a first linear pathway between the source and the detector location and blocking photons associated with a pathway disposed at an angle to the first pathway.

For example, a rejection assembly, including at least one rejection element, e.g., a blinder element, may extend into the second pathway to block associated photons from reaching the detector location. The scatter rejection assembly is preferably positioned and/or operated so as to minimize interference with the desired imaging signal while effectively reducing the effects of scatter. In this regard, a rejection element of the assembly is preferably separated from the first pathway. The height of the rejection elements is determined as a result of a trade-off optimization between several system parameters, including air-gap and image spatial resolution. For anticipated digital slot scan mammography applications, it is anticipated that the height may be at least about 5-10 mm.

In certain implementations, the rejection element is disposed wholly outside of an imaging area defined by the source and an active detector area. Alternatively, the rejection element may be partially inside the imaging area. The rejection element preferably includes a surface that is generally aligned with the first pathway between the source and the detector area. In the context of a slot scan system, the rejection assembly may have one or more surfaces where the orientation of the surface is dependent on scan location. In one embodiment, the rejection assembly is disposed at least partially outside of an imaging area and moves across an arcuate path in concert with a scan to avoid or reduce shadowing or the appearance of grid lines (at least grid-lines at a non-zero angle with respect to the scan axis).

The scatter rejection assembly may include multiple scan rejection elements. These elements may be parallel and/or transverse to one another. In connection with a slot scan system where the scanned beam has an elongate beam cross-sectional axis, the longitudinal rejection elements may be aligned with the beam axis, e.g., they may be disposed adjacent to each longitudinal edge of the beam for movement in concert with the beam scan. An associate method in accordance with the present invention involves using the scatter blocking assembly to block scattered radiation substantially without blocking any portion of the primary imaging signal, thus avoiding shadowing (or grid lines) and patient dose increase. Additionally or alternatively, the longitudinal elements may be aligned with the scan axis (or at a non-zero angle to the detector axis) to reduce the effects of scatter within the beam plane. In this regard, a grid of transverse rejection elements may be used in the slot scanning context. For example, a stationary arcuate (e.g., partial spherical) grid may be used. Alternatively, such a grid may be mounted for movement in concert with the scan so as to reduce or substantially eliminate shadowing or grid lines at any non-zero angle with respect to the scan axis. In accordance with another aspect of the present invention, a utility is provided for using exposure time imaging parameter measurements for processing the associated imaging information. Such imaging parameters include patient dependent parameters and imaging signal parameters that may vary on a procedure dependent basis such as signal intensity, spatial intensity distribution, or associated dependent parameters (e.g., detector voltage) and tissue thickness, tissue composition, patient/detector air gap or other geometric parameters. Such imaging parameter measurements may be distinguished from artifact measurements such as measurements of signal noise, electronic noise or scatter. It has been found that measurements of such parameters during an exposure time period can advantageously be used in processing associated image information.

The associated utility involves: transmitting a photonic imaging signal relative to the area of interest during an exposure period of a radiographic procedure; with the patient in position for the procedure, measuring at least a first imaging parameter value and a second imaging parameter value; detecting at least portions of the photonic imaging signal from the area of interest and providing imaging information based thereon; and operating a processor to process the imaging information using the first and second imaging parameter values. The imaging parameter values may be used for a variety of purposes including optimizing digital image quality, display, and digital diagnostic processing and scatter compensation.

The imaging parameter measurements may be imaging signal parameters measured at different times and/or different locations during the exposure period. For example, in the context of slot scan imaging, values representative of the intensity of radiation impinging on the detector at different times/scan locations of the scan can be measured. In scanning or other contexts, values representative of the intensity of radiation impinging on the detector at different locations can be measured. Such intensity measurements may be used to develop a spatial profile of the imaging signal relative to one or more axes of the imaging area. This spatial profile may be used for a variety of purposes, including scatter compensation, as described below.

Alternatively or additionally, the imaging parameter measurements may yield geometric imaging parameter values obtained either within or outside of the exposure period. For example, in the context of mammography, the geometric variables that may be measured include breast thickness (e.g., based on the engaged position of a compression paddle), tissue composition/density (e.g., based on compression force or a resistance profile obtained relative to progressive engagement of a compression paddle), and air gap distance between the compressed breast and the detector. Again, such measurements may be used for a variety of purposes, including scatter compensation, as described below.

According to a further aspect of the present invention, a utility is provided for measuring an imaging parameter value in an imaging system. The utility involves transmitting an imaging signal from an imaging source to a detector, disposing a signal attenuator between the source and detector and measuring an imaging parameter based on a signal portion transmitted through the signal attenuator. The signal attenuator may have attenuation characteristics that vary on a spatially dependent basis. For example, a signal attenuating material having a varying thickness, such as an acrylic wedge, may be disposed in a desired position relative to the detector. Alternatively, a window of varying opacity may be provided for this purpose. The varying attenuation facilitates accurate measurements, including comparative measurements, under a variety of imaging conditions without saturation (e.g., exceeding the dynamic range of analog-to-digital converters or other processing components), thereby accommodating exposure period measurements or other measurements where the system settings may be determined at least in part by factors other than the attributes or limitations of the imaging parameter measurement components.

In one implementation, one or more such signal attenuators are used in the slot scanning context. For example, a longitudinal acrylic wedge having its major axis aligned with the scan axis may be used to allow for intensity measurements over the course of a scan. In this manner, scan position dependent intensity variations, e.g., due to source fluctuations or detector alignment errors, can be identified and used for any of various purposes. The major axis of such a wedge may alternatively be oriented transverse to the scan axis to characterize a beam profile relative to that axis. The combination of scan axis and transverse attenuators allows for characterization of a two-dimensional profile of the imaging signal impinging on the organ/object to be imaged as may be desired.

According to another aspect of the present invention, an "air gap" between a patient and a detector surface is selected to reduce the effects of scatter. The associated utility involves establishing a mathematical model for modeling a magnitude of expected scatter detection as a function of a distance between tissue being imaged and a detector surface, and using the mathematical model to set a distance between a tissue support structure and the detector surface. This distance may be varied for particular imaging procedures based on other parameters such as tissue thickness and composition, and is optimized as a function of several imaging system performance including image contrast and spatial resolution. Alternatively, a fixed spacing between the tissue support and detector surface may be optimized based on a range of expected imaging parameters. According to a related aspect of the invention, a mammographic imaging system has a spacing between a breast support and a detector surface of between about 1-mm and 40-mm and, more preferably, between about 2-mm and 30-mm.

According to a still further aspect of the present invention, a utility is provided for compensating for the effects of the scatter, taking into consideration both single and multiple scatter. The utility involves: transmitting radiation into a selected tissue region of a patient's body; detecting radiation from the selected tissue region of the patient's body, wherein the detected radiation includes a scattered portion and a non-scattered portion; estimating first and second parts of the scattered portion, wherein the first part corresponds with photonic energy passing through the selected tissue region with a single scattering occurrence and the second part corresponds with photonic energy passing through the selected tissue region with multiple scattering occurrences; obtaining radiographic image data in relation to the detected radiation from the selected tissue region; and utilizing the estimated first and second parts of the scatter portion to adjust the radiographic image data. The step of estimating the first and second parts of the scattered portion may be based on a mathematical model. The model may address Compton scatter effects as well as Rayleigh scatter effects. Additionally, the model may utilize any of a variety of imaging parameters including, for example, a measured dimension of the tissue region, a tissue composition or density of the selected tissue region, a power setting for the radiation source (with associated, known source emission spectra), a measured intensity of detected radiation, and an intensity profile of detected radiation or the like. These values may be determined for a particular radiographic procedure and, more particularly, may be measured at one or more times during an exposure period of the radiographic procedure.

According to another aspect of the present invention, scatter compensation is performed based on procedure specific imaging parameter measurements. The associated utility involves: transmitting radiation into the selected tissue region; detecting radiation from the selected tissue region, where the detected radiation includes a scattered portion and a non-scattered portion; positioning a patient in a desired position for a radiographic procedure; with the patient positioned in the desired position, operating a parameter measurement device to measure a procedure specific value of a scatter related parameter and provide an output indicative thereof; obtaining radiographic image data in relation to detected radiation from the selected tissue region; and operating a processor to receive the output from the parameter measurement device and use the image specific value of the scatter related parameter to adjust the radiographic image data. For example, the scatter related parameter may be an imaging parameter such as one or more values relating to the intensity of the transmitted or detected radiation, or the parameter value may be a geometric parameter relating to the tissue thickness or composition or the spacing between the tissue and the detector. The value may be measured during an exposure period of the radiographic procedure or otherwise with the patient positioned for the procedure. In this manner, procedure specific values are measured for improved scatter compensation.

According to yet another aspect of the present invention, a utility is provided for performing scatter compensation in connection with a composite imaging system. As noted above, such composite imaging systems may provide advantages related to scatter rejection. Scatter performance can further be enhanced by providing scatter compensation in connection with such a composite imaging system. Thus, an associated utility involves: transmitting a photonic imaging signal relative to an area of interest of a patient's body during an exposure period of a radiographic procedure; first operating a detector to detect portions of the imaging signal from the patient's body and provide a detector output indicative thereof, where the detector output reflects imaging information for different portions of the area of interest obtained at corresponding different times of the exposure period; establishing scatter compensation information for the radiographic procedure; and operating a processor to process the detector output using the scatter compensation information so as to provide reduced scatter composite imaging information of the area of interest. Preferably, the scatter compensation information is based on a mathematical model for scatter compensation that uses measurements of one or more scatter parameters. These scatter parameters are preferably measured on a procedure specific basis and may include exposure time measurements. Additionally, the scatter compensation information may take into account single and multiple scatter including both Compton and Rayleigh scatter effects. Parameters of the scatter estimation models may be optimized as a result of extensive imaging of various test objects, including anthropomorphic phantoms, as well as clinical investigations.

According to another aspect of the present invention, a composite imaging system such as a slot scanner is implemented with an imaging beam having a scan axis dimension no greater than a corresponding dimension of an active detector area. Heretofore, such composite imaging systems have generally employed over-collimated beams, i.e., beams having a cross-sectional scan axis dimension (width) greater than the detector width, in order to avoid scan axis intensity modulation and associated display artifact due to, for example, beam/detector alignment variations during the scan. Such alignment variations may be caused, for example, by scan drive fluctuations. Such overcollimation may result in greater patient dosages and increased scatter potential.

The present invention includes a utility utilizing a matched or undercollimated beam. The utility involves: a source system for transmitting an imaging beam; a detector for detecting the beam from the area of interest of the patient's body and providing an output that includes imaging information for different portions of the area of interest obtained at different times; and a processor for processing the detector output to provide composite imaging information for the area of interest. The source system and detector are configured such that a dimension of the beam at the detector surface, relative to a first axis, is no greater than the corresponding dimension of an active detector area. In this regard, the source system may include a collimator for providing the desired beam width. This configuration may allow direct detector measurements of the scatter-only radiation, and either direct estimation of the scatter in the primary field (via interpolation) or refinement of the scatter estimation model parameters via fitting of the estimates to the actual measured values in the scatter-only field. Any drive related intensity fluctuations can be reduced by appropriate mechanical elements for stiffening the drive, electrical elements for appropriate modification of a drive signal, and/or sensor elements to identify exposure period intensity variations so as to allow for compensation during processing. In this manner, potential reductions in patient dosage and scatter can be achieved.

BRIEF DESCRIPTION OF THE DRAWINGS

For a more complete understanding of the present invention and further advantages thereof, reference is now made to the following Detailed Description taken in conjunction with the drawings, in which:

FIGS. 5A and 5B are front and side cross-sectional views, respectively, of a detector assembly in accordance with the present invention illustrating certain scatter paths;

DETAILED DESCRIPTION

In the following description, the invention is set forth in the context of a digital, x-ray slot-scan mammography system. This represents a particularly advantageous implementation of the invention as mammography is a challenging medical imaging application, in terms of both required contrast and resolution, and digital slot-scanning provides a number of advantages as discussed above related to reduced scatter, reduced dosage, enhanced resolution and digital display enhancement. However, various aspects of the invention are more broadly applicable in other contexts including other medical imaging applications.

The following discussion first provides a description of a digital slot-scan mammography system. Thereafter, various system components for reduced scatter generation and improved scatter rejection are described, i.e., system adaptations to reduce the amount of scattered photonic energy detected at a detector surface. Finally, various system adaptations and processing techniques are disclosed for obtaining enhanced image-related information including scatter compensation, e.g., adjusting detected values to compensate for scatter effects.

1. Slot-Scan System

Figure 1:
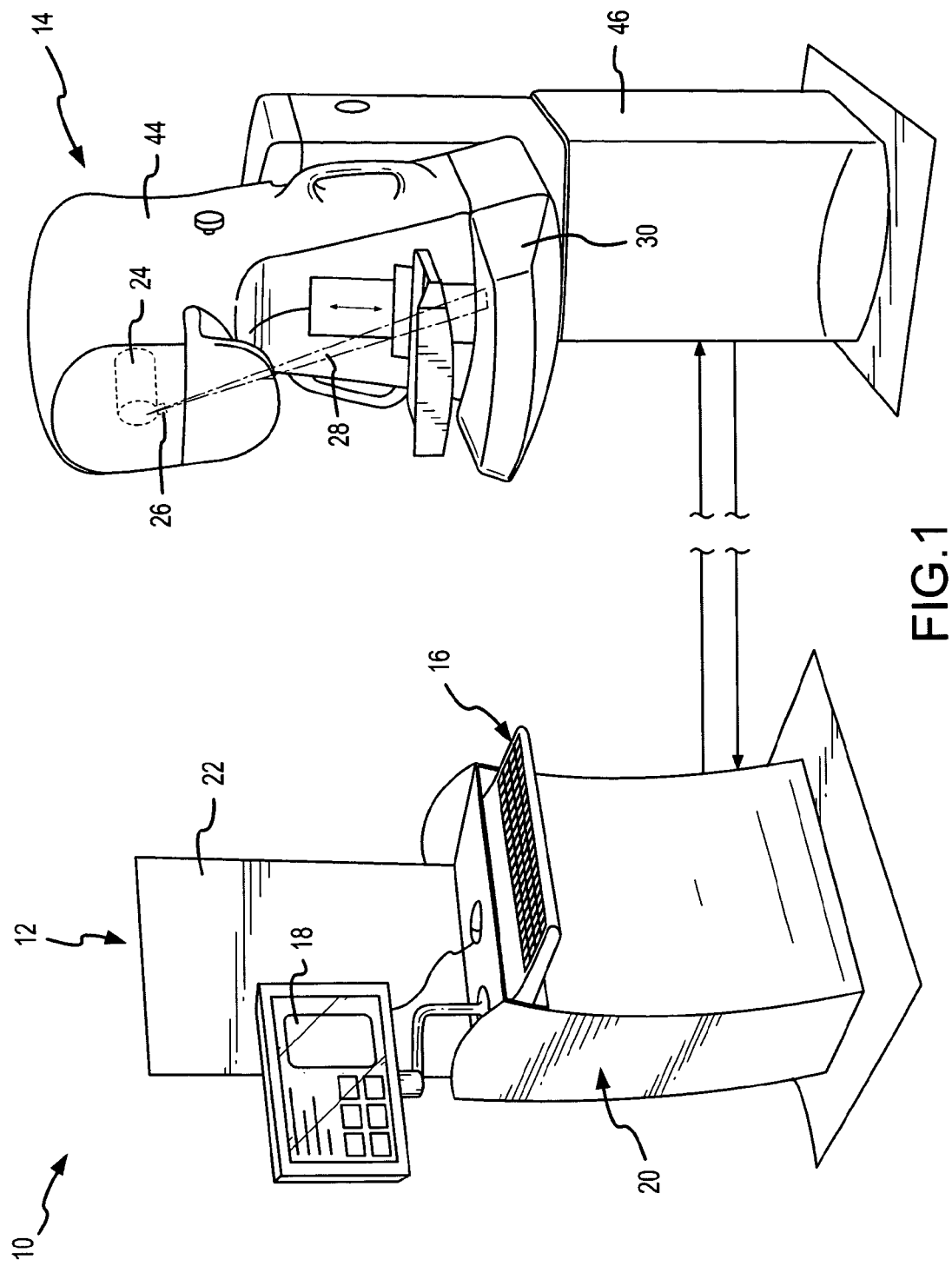
FIG. 1 is a perspective view of a slot-scan digital mammography system in accordance with the present invention.

FIG. 1 illustrates one embodiment of a slot-scan system 10 which may be utilized in implementing the present invention. The operation of such a system is described in detail in U.S. Pat. Nos. 5,917,881 and 5,526,394, assigned to Fischer Imaging Corporation, which are incorporated herein by reference. The system 10 includes a monitoring station 12 and imaging station 14 operatively interconnected thereto. The monitoring station 12 may be located adjacent to the imaging station 14 as shown or at a remote location. The illustrated monitoring station 12 includes a user interface 16 such as a keyboard, mouse or the like (e.g., for entering patient data), a user interface display 18 (e.g., for displaying/selecting/accepting images), and a processor 20 interconnected to the user interface 16, user interface display 18 and imaging station 14. Processor 20 is adapted to receive, process and store image signals generated at the imaging station 14 and other image related information, as will be discussed in detail below, and to control various operations at the imaging station 14. The monitoring station 12 may also include a radiopaque and optically transparent shield 22 for shielding medical personnel during observed patient imaging operations at the imaging station 14. Various processing functions are described below including image time or post acquisition processing to compensate for scatter. It is noted that various aspects of such processing may be performed by a separate processor such as at a remote image review station. Moreover, such processing may be distributed over multiple platforms, for example, to enable a server with substantial computing resources to support multiple image acquisition and/or review stations at one or more medical facilities. In other cases, a stand-alone unit may provide all of the processing functionality. The illustrated imaging station 14 includes an x-ray radiation source 24, e.g., an x-ray tube with collimating and filtering optics 26, for transmitting a narrow radiation beam 28. The radiation source 24 may be disposed for controlled rotation about its longitudinal axis, wherein the radiation beam 28 may be scanned across a selected region of a patient's body, in this case, a compressed breast. A detector assembly, as described below, is housed within detector housing 30.

Figure 2:
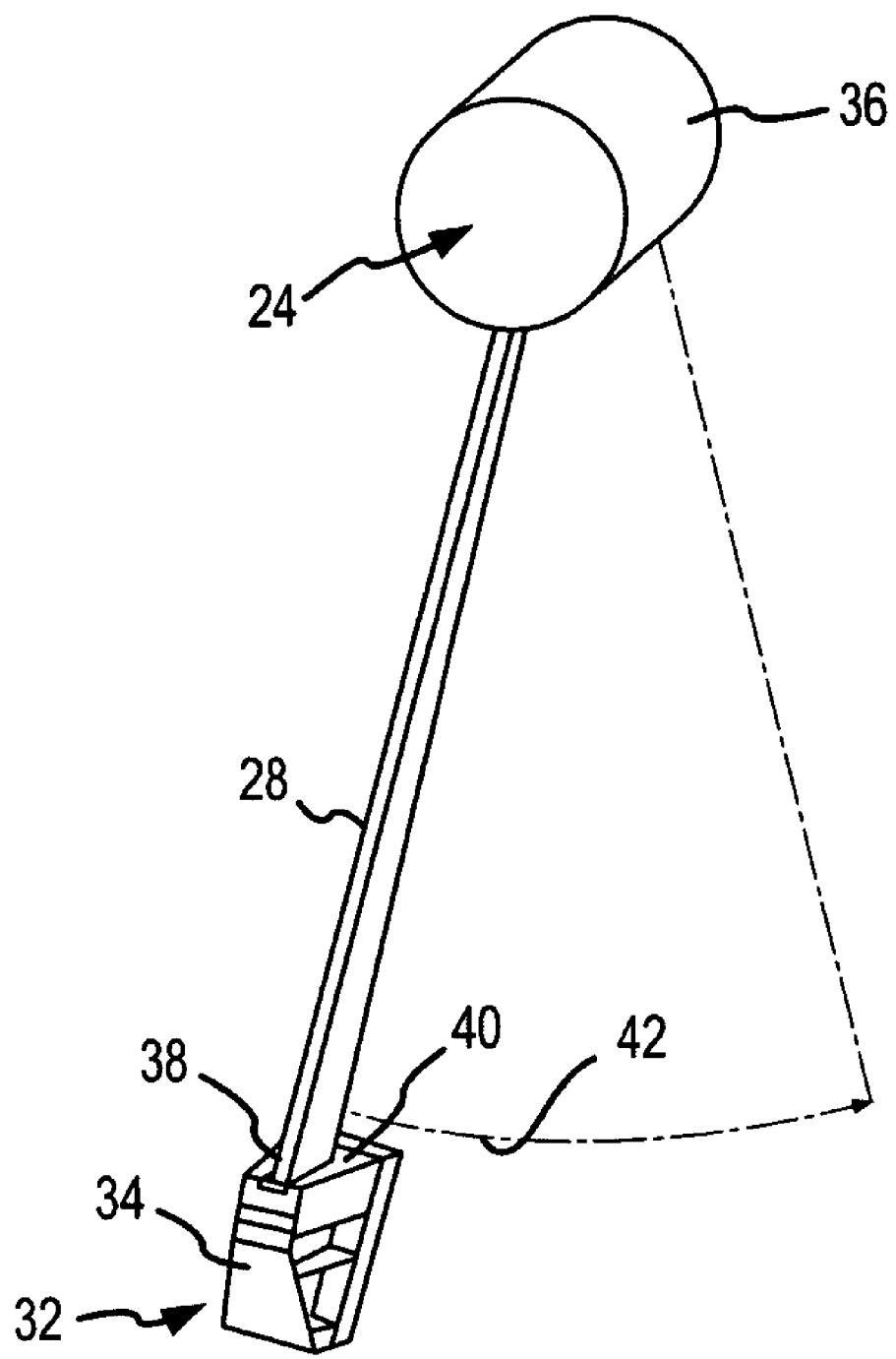
FIG. 2 illustrates the scanning motion of the imaging system of FIG. 1.

The scanning motion of the beam 28 is illustrated in FIG. 2. Specifically, the beam 28 is shown in bold at one end of a scan motion, and in shadow at other points of the scan motion. FIG. 2 also shows a detector assembly 32 that is housed within the housing 30 of FIG. 1. The detector assembly 32 preferably includes an active detector area 38, for receiving the beam 28 and providing an electrical output indicative thereof, that closely corresponds in size and shape to the cross-section of the beam 28 at the surface of the active detector area. As discussed above, composite imaging systems such as the illustrated slot-scanning arrangement have inherent scatter rejection advantages, as much of the scattered radiation will not be detected. The present invention may be advantageously implemented in connection with such systems.

In this regard, such an active detector area 38 is moved in concert with the beam 28 through the scan motion so as to continuously receive the beam 28. Such movement may be accomplished by electronically moving the active portion of a large stationary detector. Alternatively, and as shown, the detector may be physically moved through the scan. Specifically, the illustrated detector assembly 32 includes a shuttle structure 34 that carries a narrow detector area 38 as will be described in detail below. The shuttle structure 34 is associated with a head structure 36 of the source 24 such that the shuttle structure 34 travels through an arc or other path as the head structure 36 rotates about an axis of rotation.

The shuttle structure 34 and head structure 36 may be driven through this scan in any appropriate way. Preferably, the structures 34 and 36 are co-driven to facilitate concerted motion of the beam 28 and active detector area 38. In this regard, the structures 34 and 36 may be interconnected such that driving one of the structures 34 or 36 results in coordinated movement of the other. A telescoping interconnection structure or other arrangement may be provided to allow for varying the distance between the structures 34 and 36 as may be desired. In the illustrated embodiment, a motor 40, such as a microstep motor, is carried by the shuttle structure 34. A spindle is mounted on an output shaft of the motor to roll on cam surface 42. Thus, driving the motor 40 in response to a drive signal from a controller associated with the processor 20 (FIG. 1) causes the spindle to wind scan cables affixed to the gantry . . . which, in turn, drives the shuttle structure 34 through the scan arc and rotates the head structure 36.

Referring again to FIG. 1, the imaging station 14 may be utilized to obtain various imaging views in relation to the patient's immobilized breast defined, for example, by the beam axis at the centerpoint of a scan. To allow for such views, the illustrated station 14 includes an imaging unit 44 rotatably mounted on a pedestal 46. Pedestal 46 enables motorized elevation of the imaging unit 44 along a vertical axis. The imaging unit 44 includes the source 24, detector housing 30 and other components mounted on a common support structure. This support structure is mounted for rotation about an axis extending between the imaging unit 44 and the pedestal 46. Optionally, the imaging unit 44 may also be tiltable relative to a vertical plane. Such motions may be motorized to automatically position the imaging unit 44 in response to inputs entered at the monitoring station 12 or elsewhere on the imaging station, and a brake mechanism may be provided to lock the unit 44 in the desired location.

Figure 3C:
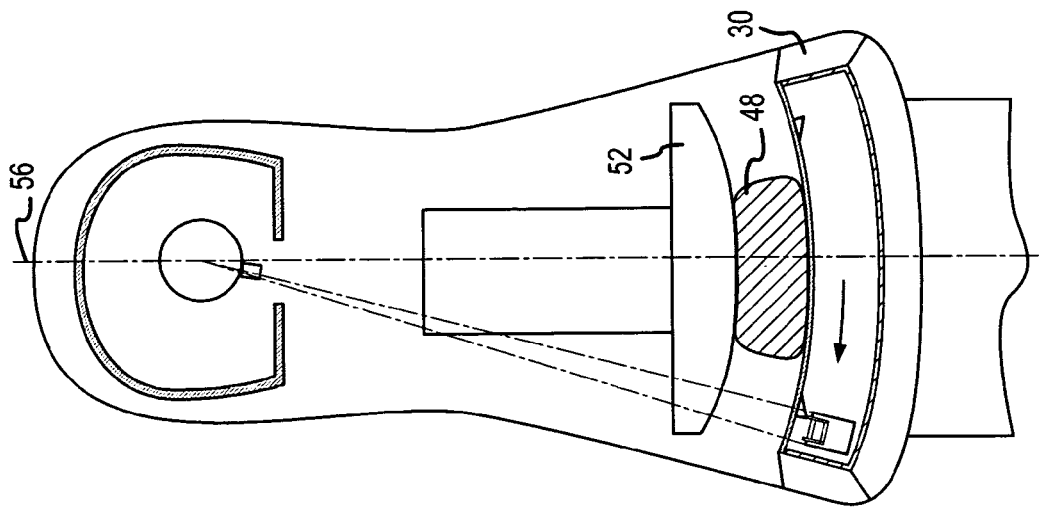
FIGS. 3A-3C are front cross-sectional views illustrating the scanning motion of the system of FIG. 1.
Figure 3B:
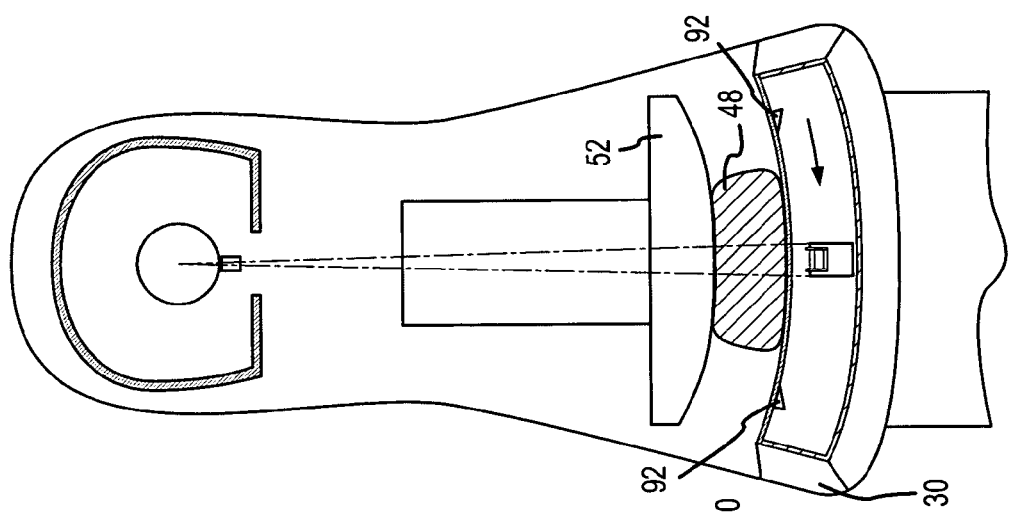
Figure 3A:
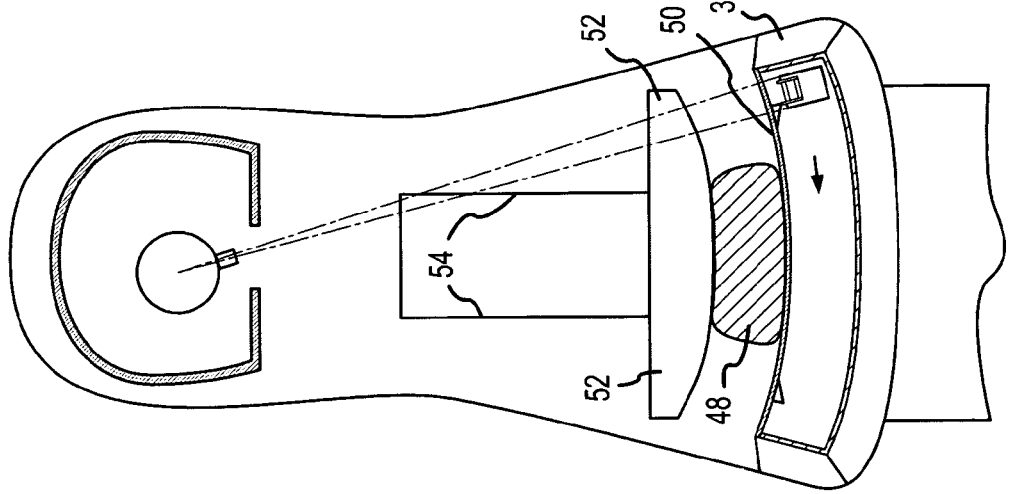

FIGS. 3A-3C illustrate an image acquisition process in relation to a patient's compressed breast 48. The patient's breast 48 is compressed for the procedure to provide a more uniform thickness and to immobilize the patient for improved imaging. In the illustrated embodiment, the patient's breast 48 is captured between an upper surface 50 of the detector housing 30 and compression paddle 52. The illustrated paddle 52 is arcuate in shape such that a more uniform tissue thickness is provided across the scan motion and is formed from radio-transmissive material. In addition, the paddle 52 is movable on tracks 54 relative to an imaging axis 56 (coinciding with a center axis of the scan motion). Such motion may be motorized. Moreover, a release may be provided to allow the paddle 52 to be quickly disengaged from the patient's breast 48 as may be desired.

Figure 4:
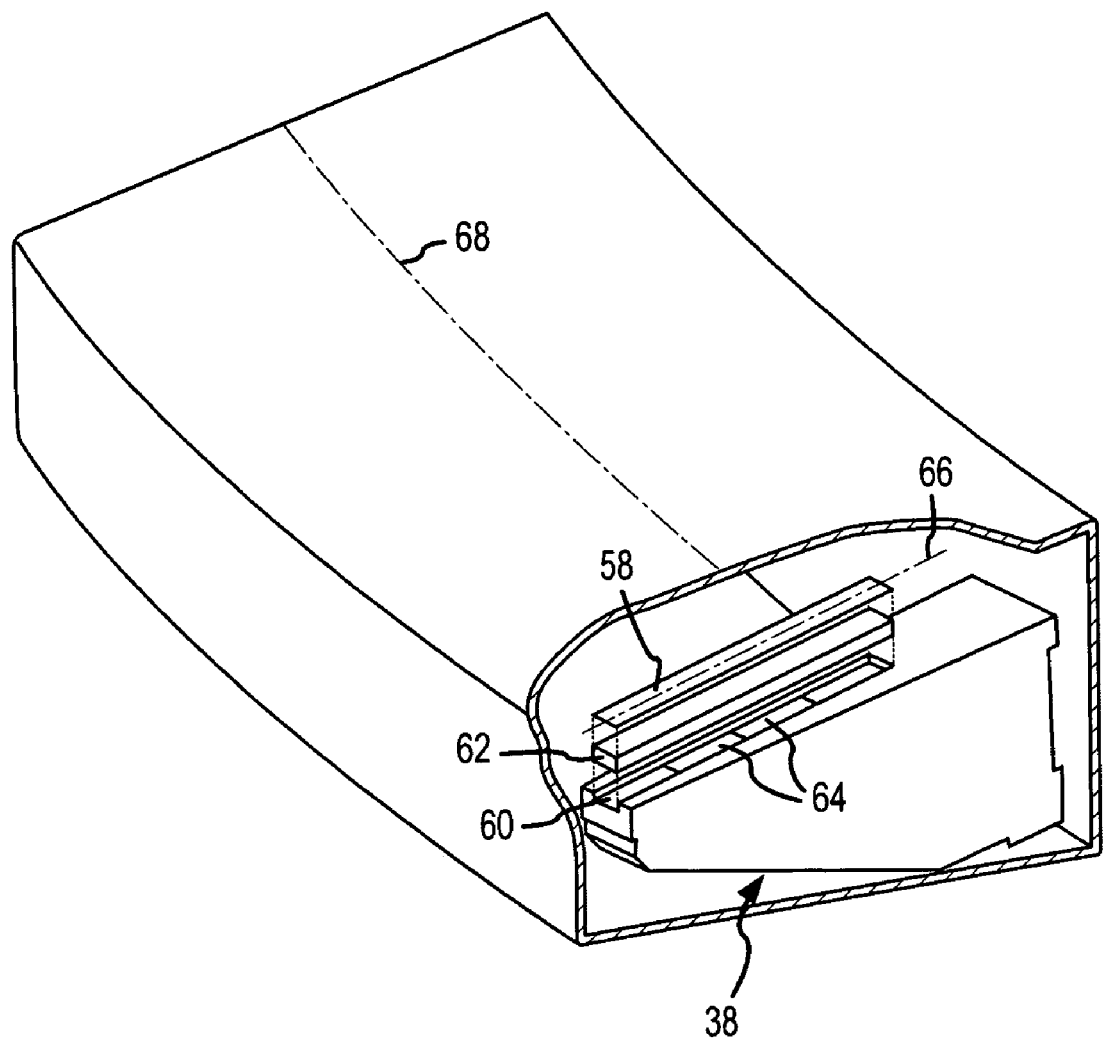
FIG. 4 is a perspective partial cutaway, partially exploded view of a detector assembly of the system of FIG. 1.

FIG. 4 shows details of the active detector 38 within the housing 30. As noted above, the active detector 38 provides an electrical output representative of detected radiation. In this regard, x-ray radiation may be directly detected or spectrally transformed prior to detection. The illustrated detector 38 includes a scintillator strip 58 for emitting and transmitting light in response to incident x-ray radiation and a detector strip 60 for detecting the light. The scintillator strip 58 is optically coupled to detector strip 60 via a fiber optic plate 62. The illustrated detector strip 60 is formed from four detector surfaces 64.

The detector strip 60 defines an array of detector elements. These elements may form, for example, a single line of elements or multiple lines of elements aligned with a major axis 66 of the array, also referred to as the detector axis. For example, these elements may be provided as part of a CCD array or other photoelectric transducer array. In the case of a single line array, values proportional to accumulated charge may be read out from each element at a frequency selected to provide the desired resolution in relation to the detector motion along the scan axis 68. In the case of multiple lines, a time delay integration process may be implemented by shifting charge across the array in synchronization with the scan motion for read out at the trailing edge of the array (alternatively signals may be combined digitally, "off-chip"). This enables charge to be integrated for the full beam width without sacrificing resolution, thereby enabling practical imaging with available x-ray sources. For example, such synchronization may be achieved by linking charge shifts to pulses of a microstep motor driving the scan or the output of an encoder associated with the moving detector (or other moving component). It is apparent that this slot-scan geometry will result in reduced scatter generation and substantial scatter rejection. However, certain enhancements are possible to further improve such scatter avoidance as discussed below.

2. Scatter Avoidance

The present invention provides high-resolution medical images (for example, digital mammographic images) by very significantly reducing the amount of detected scatter that contributes to such resultant images. The amount of scatter contributing to a radiographic image typically depends primarily on the amount of scatter generated during image acquisition and the proportion of generated scatter that is detected by the detection assembly. While the angular distribution of scatters (due to the Compton and Rayleigh effects) may vary somewhat with energy (e.g., intensity of the radiation), at first approximation the Compton scatters may be considered to be uniformly distributed at a given angle (that is, isotropically distributed). By contrast, the Rayleigh scatter tends to be more "forward-peaked" due to the maintenance of the photonic energy associated with this phenomenon. In both cases, the proportion of scatters generated at a given site and recorded in the resultant image may be characterized as depending on a solid angle defined by the detector assembly and the scatter location. This "solid angle" generally corresponds with a distance from the scattering center to the detector (the solid angle decreases with the square of the distance, hence the effectiveness of air-gaps in reducing scatter in x-ray images), and on the detector area.

The narrow detector used in slot-scanning, and therefore the much reduced detector area, explains the effectiveness of this technology in rejecting scatter. For example, for a 6-cm compressed breast of 50/50 composition (50% fibro-glandular and 50% adipose), the scatter-to-primary ratio (the quantity of interest in medical imaging that determines the amount of contrast reduction introduced by scatter) is of the order of 15%, or comparable to what could be achieved using only a conventional grid. Moreover, the present invention, as an alternative to solely using traditional grid designs, beneficially leads to significant intrinsic dose savings. This means that the patient is exposed to less radiation (relative to conventional imaging processes) during image acquisition. Further, lower intrinsic doses allows for higher (or "tighter") spatial resolution with high signal-to-noise ratios. That is, lower impinging radiation intensity levels, in combination with the reduction in scatter contributing to the resultant image, allow for sharper or clearer radiographic images at a given patient dose level.

For any scatter point in the breast being imaged, the small detector area leads to a small probability of detection. The mean a free path of an x-ray in tissue is dependent upon the tissue attenuation coefficient and the x-ray energy. Considering a mean energy of 20-kev, and a corresponding attenuation coefficient of the order of 0.5 per cm, the mean x-ray free-path is of the order of 2-cm. It is therefore seen that as the breast thickness increases, the likelihood of a given x-ray being scattered more than once increases. For both analysis and scatter reduction considerations, it is useful to separate scatters in two categories, single scatters (having been scattered or deflected once) and multiple scatters. Due to the geometry of a slot-scanning system, it is clear that all single scatters detected originated within the breast volume illuminated by the beam (at a given instant). It is also clear that multiple scatters detected are very unlikely to have had their last scatter event within the illuminated volume (this follows directly from the solid angle geometric consideration above, and from the fact that multiple scatters may be considered isotropic in first approximation). Accordingly, a large portion of potentially detected multiple scatters will be directed to the detector at an angle with respect to the beam plane (the plane including the focal spot and the detector axis edge of the breast support). It is therefore apparent that two parallel collimator slats on either side of the active detector area may be effective in reducing the detection in multiple scatters, while having no effection the detected primary beam.

Figure 5B:
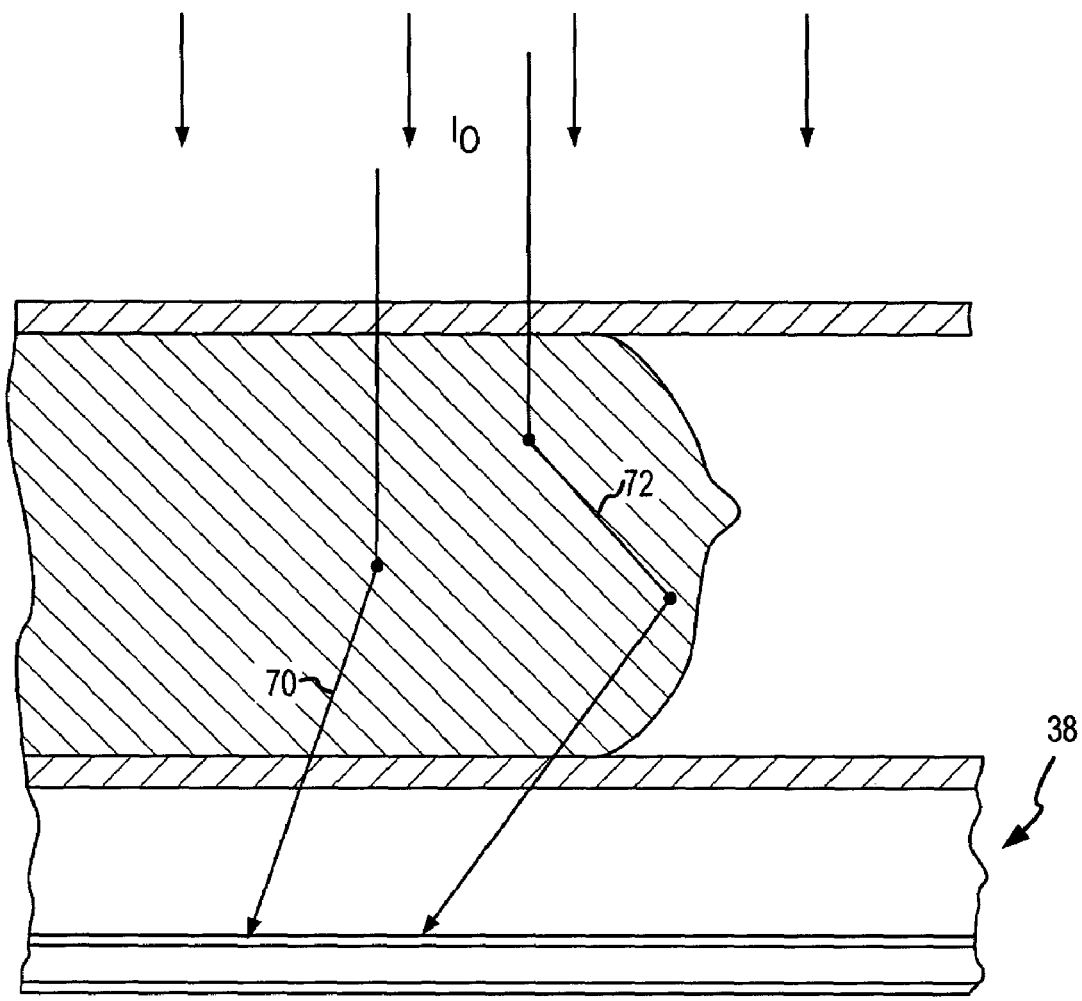

This is illustrated in FIGS. 5A and 5B where $I_0$ indicates an illuminating intensity of the imaging beam 28. A primary portion P of the beam 28 traverses the patient's breast 48 and impinges on the active detector area 38. Pathways 70 illustrate single scatter; that is, photonic energy passing through the patient's breast with only a single scatter occurrence. Paths 72 illustrate multiple scatter. It will be appreciated that, depending on the type of scatter involved, the pathways 70 and 72 may be defined by the motion of one or more than one photon. As shown, a small portion of single scatter 70 will be directed to the active detector area 38 as a result of the slot-scan geometry. Most of the multiple scatter 72 will be directed to the active detector area 38 from outside of the illuminated portion of the patient's breast 48.

In the illustrated embodiment, collimator slats 74 are provided at the leading and trailing edges (defined in relation to the scan motion) of the active detector area 38. The collimator slats 74 extend a height, h, above the detector's surface relative to the beam axis 75 (center axis of the beam) and are formed from a material suitable for absorbing or blocking x-ray radiation. These slats 74 extend into the pathway of certain scattered radiation 72 to reject the radiation. In particular, the slats 74 will reject radiation having an incidence angle less than a rejection threshold measured relative to the plane of the detector surface. The rejection threshold depends on the height of the slats and the points on the detector under consideration. Generally, however, the effectiveness of the slats 74 in rejecting scatter will depend on the height h in relation to the width, w, of the active detector array. In this regard, the height, h, is preferably at least 50% and more preferably at least 100% of the width w. In the illustrated embodiment, the width, w, is about 10 mm and the height h is about 10 mm. It will be appreciated that the slats 74 are particularly effective in rejecting multiple scatter (originating mostly in large breasts).

Another factor that affects the amount of scatter detected is the width of the x-ray beam. In particular, the amount of scatter generated is proportional to the volume of tissue illuminated by the x-ray beam 28. Thus, scatter can be reduced by narrowing the beam 28, while keeping the detected primary intensity unchanged for a given technique. However, conventional slot-scan systems have generally utilized overcollimated beams, i.e., beams having a width in excess of the active detector width. Such overcollimation accommodates relative motion between the beam 28 and active detector area that might otherwise result in modulation of the detected intensity. Thus, for example, for an active detector area that is 10 mm wide, a 12 mm beam width at the detector would allow for 1 mm of beam motion with respect to each side of the detector. The penalty for such overcollimation would be a 20% dose increase as compared to the dose that contributes to image formation as well as an increase in scatter generation, as well as a 20% increase in scatter generation (and thus in S/P) as compared to a 10-mm wide beam for the same amount of detected energy.

Figure 6:
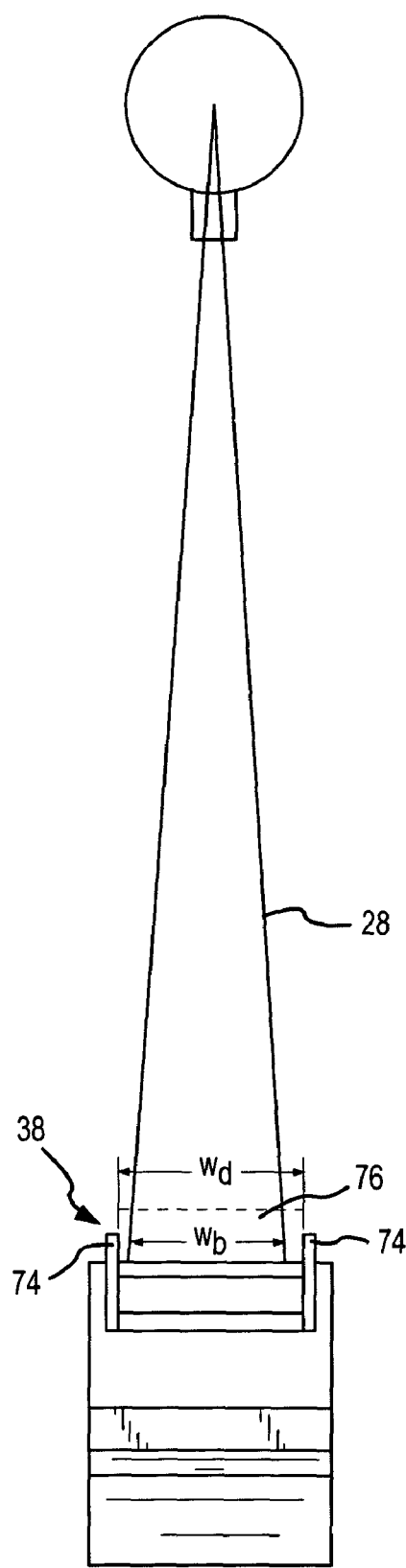
FIG. 6 is a front view showing the geometry of the source and detector system in accordance with the present invention.

The present invention may utilize a matched or undercollimated beam as illustrated in FIG. 6. Specifically, the width of the beam at the detector surface, $w_b$, is no greater than the width of the active detector area, $w_d$. In this regard, narrowing the beam 28 reduces scatter generation but also, in the case of undercollimation, the beam width over which charge integration can occur. Accordingly, $w_b$ is preferably between about 0.7 $w_d$ and 1.0 $w_d$ and, more preferably, between about 0.9 $w_d$ and 1.0 $w_d$. Moreover, to ensure adequate exposure in the case of undercollimation, the x-ray source preferably provides and output of at least about 150 mA in the range of 26-32 kVp and, more preferably, an output of at least about 200 mA in the noted range. The illustrated embodiment uses a rad 71s tube. The illustrated embodiment also utilizes a high efficiency scintillator for optimized DQE, image quality, and high-resolution imaging. It has been found that intensity modulation due to relative motion between the beam 28 and the active detector surface 38 is most pronounced at the beginning and end of the scanning motion, i.e., associated with scan acceleration. It is noted that such modulation is of little practical significance in the context of mammography as the ends of the scan motion are generally outside of the image area of interest. Nonetheless, such potential image artifacts can be addressed by varying the drive signal to the scan motor. In particular, such intensity modulation can be empirically modeled to identify relative motion transients. These transients can be used to develop a modified ramp up and ramp down drive signal to smooth such transitions. These developed drive signals can be tested and improved to reduce the associated intensity modulation.

Such intensity modulation can also be corrected in processing by using a reference signal. Such a reference signal may be generated by profiling the detected signal relative to the scan axis. For example, during a scan, intensity measurements at the anterior edge of the array (the edge farthest forward from the patient's chest wall), which is generally outside of the illuminated tissue region, can be read out over the course of the scan and used as a reference intensity signal. Thus, based on this intensity profile, the measured intensity can be scaled or normalized on a line-by-line basis relative to the scan axis to reduce or substantially eliminate any intensity modulation due to relative motion between the beam 28 and the active detector area 38.

Figure 11A:
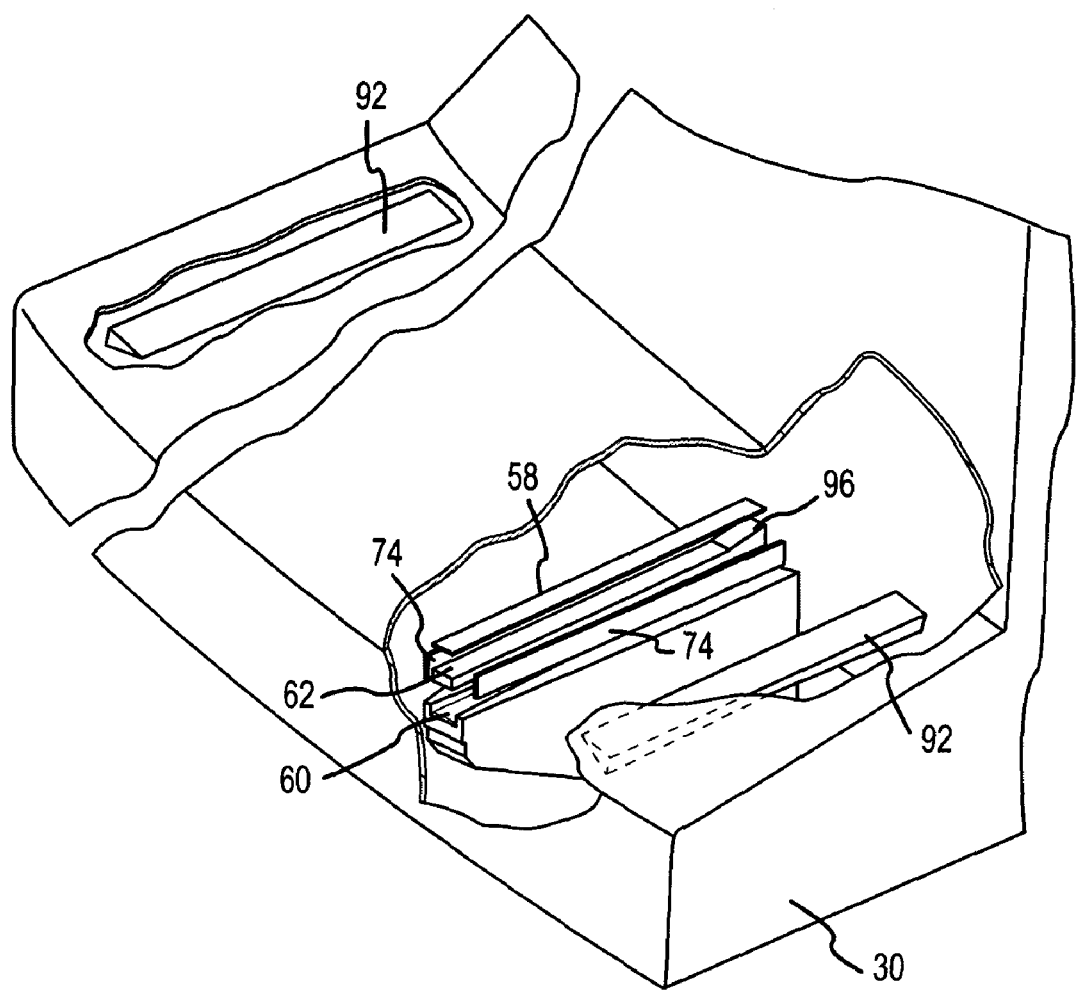
FIG. 11A is a perspective partially cutaway view showing a detector housing and related components in accordance with the present invention.
Figure 11B:
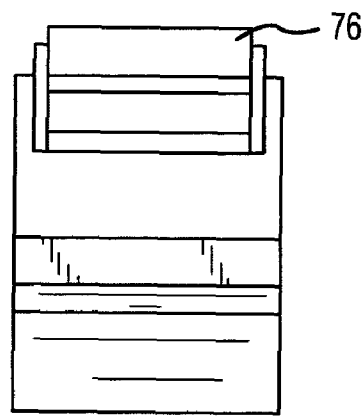
FIG. 11B is a front view showing a detector assembly in accordance with the present invention.

However, it will be appreciated that the beam portion transmitted through the patient's tissue will be significantly attenuated in relation to the beam portions detected at the anterior edge of the detector array. The amount of such attenuation will depend on, inter alia, the thickness and composition of the illuminated tissue. In order to avoid saturation and provide useful intensity profile measurements under a range of conditions, an attenuator 76 (see also FIGS. 11A and 11B) is disposed adjacent to the anterior edge of the active detector area 38. The attenuator 76 preferably has signal attenuation characteristics that vary relative to the detector axis 66 (FIG. 4) but do not vary substantially relative to the scan axis 68. Such variation relative to the detector axis 66 may be accomplished by providing a varying thickness of an x-ray attenuating material or providing a window having a varying opacity. In the illustrated embodiment, the attenuator comprises an acrylic wedge oriented to provide a varying thickness relative to the detector axis 66. In this manner, it is anticipated that a line of detector elements at some location between the narrowest and widest point of the wedge can be used to provide information for developing an intensity profile without saturation under a range of imaging conditions.

Scatter rejection can also be enhanced by controlling the size of the air gap between the illuminated tissue and the detector surface. In particular, as the Compton component of single scatter may be assumed relatively uniformly distributed in angle, while the Rayleigh component of single scatter is highly forward-peaked, it is apparent that increasing the distance between the breast support and the detector (the air gap) will significantly decrease the amount of detected Compton scatters while decreasing by a smaller proportional amount the Rayleigh scatters detected. In particular, increasing the air gap from 0 centimeters as shown in the embodiments of FIGS. 1-4, to a few centimeters will very significantly decrease the amount of total scatter detected. Moreover, based on a mathematical model as discussed below for modeling of scattered radiation, it is apparent that the air gap can be tuned according to the measured compressed breast thickness to leverage this effect. According to such model, the median plane through the compressed breast thickness is placed at distance from the detector determined from the breast thickness, composition, and imaging parameters such as kVp.

Figure 7:
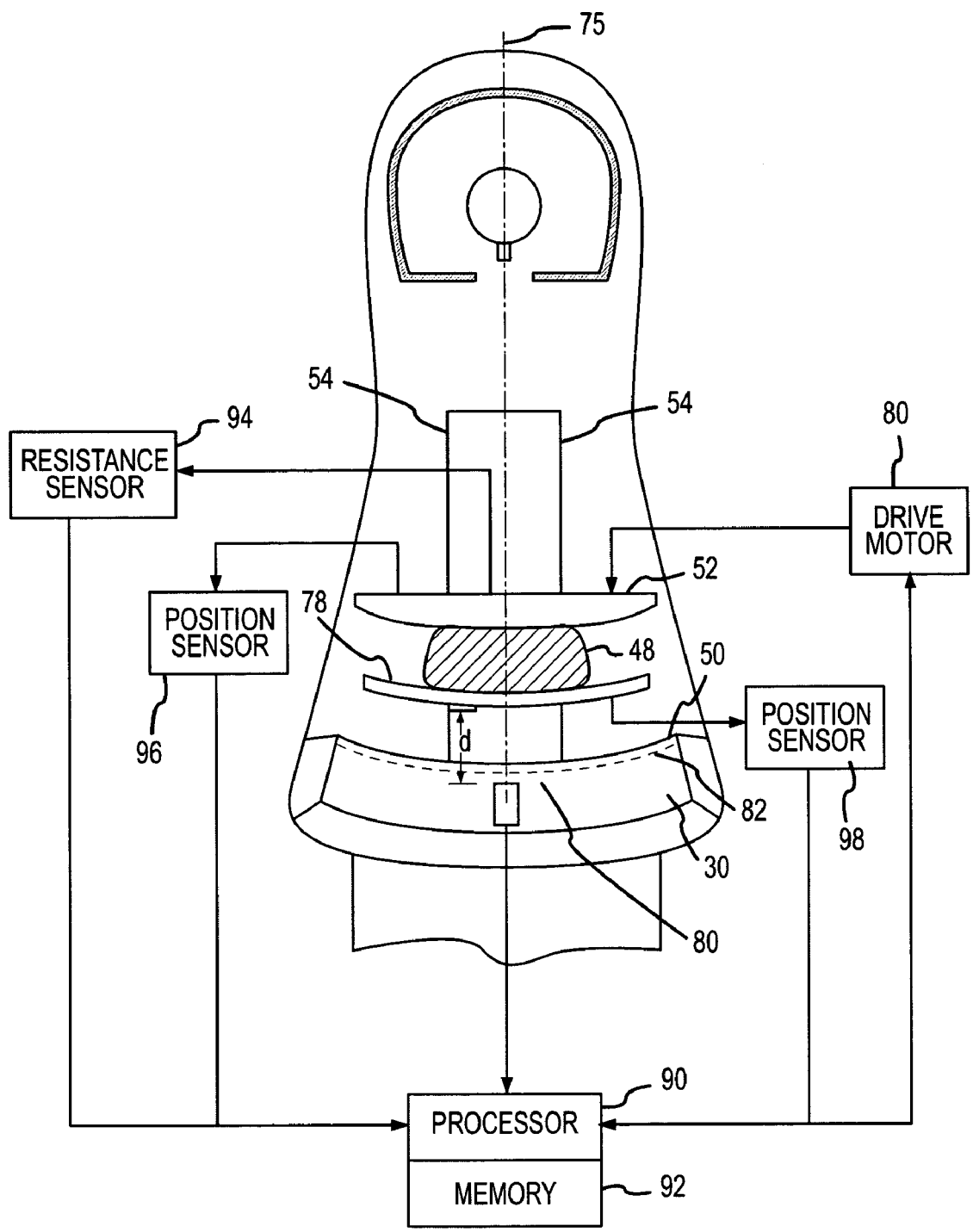
FIG. 7 is a front partially schematic view of an imaging system in accordance with the present invention.

FIG. 7 illustrates a system where such tuning can be accomplished. In the illustrated embodiment, the patient's breast 48 is not compressed against the upper surface 50 of the detector housing 30. Rather, the patient's breast 48 is supported by a support plate 78 that is separated from the upper detector surface 80 by a distance d. This distance may be variable or may be fixed. In the case where this distance is fixed, the magnitude of this distance may be tuned relative to an average expected tissue thickness. For example, in the case of mammography, d is preferably between 5 and 30 and more preferably between 10 and 20-mm. The support plate 78 is preferably curved so that this distance is substantially constant throughout a scan.

In the illustrated embodiment, this distance may be varied by moving the support plate 78 and/or the detector housing 30 and/or the detector within the housing along the beam axis 75 on tracks 54. In this regard, moving the housing 30 has the advantage that the air gap can be selected after the tissue thickness has been measured without moving the patient. However, moving the housing 30 (or the detector within the housing) is structurally more difficult to implement and results in a varying beam width at the detector surface 80. Thus, in operation, the patient's breast 48 may first be positioned on the lower support plate 78. The compression paddles 52 may then be manually or automatically lowered to compress the patient's breast 48. Once the breast 48 is compressed in an imaging position, the thickness of the patient's compressed breast 48 may be measured, e.g., based on markings associated with the paddle 52 or based on an output signal from a paddle drive motor 80 or an encoder. This value can then be provided to the processor 20 (FIG. 1) which determines an optimal air gap. The lower support plate 78 and/or the detector housing 30 may then be manually or automatically moved to establish the desired air gap for optimized scatter rejection. The breast support plates and gantry elevation motions may be simultaneous and in opposite directions, so that as a result the absolute patient position in three-dimensional space is unchanged.

Figure 8:
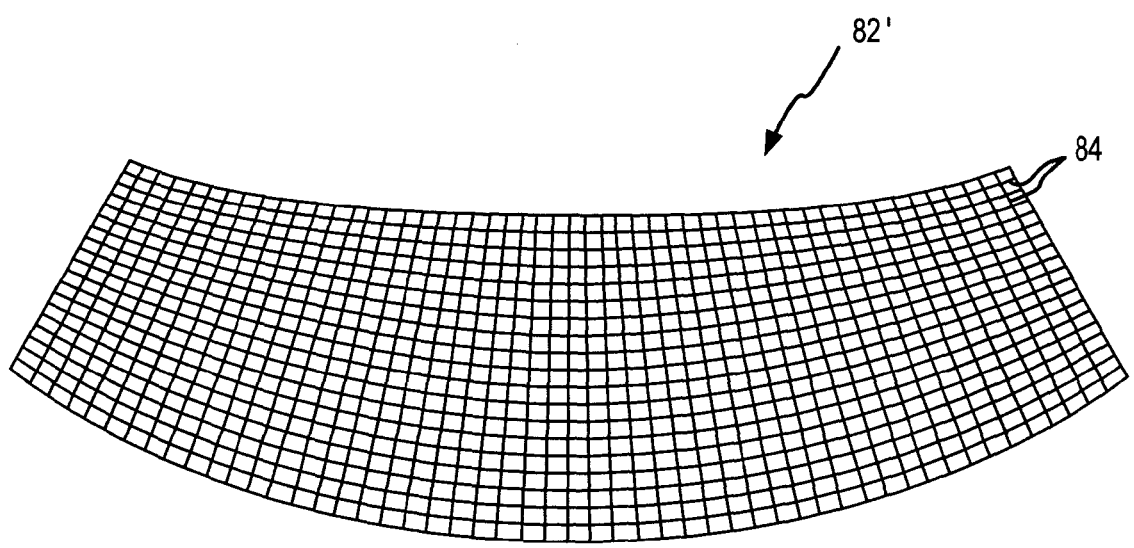
FIGS. 8-10 show various grid configurations for use in accordance with the present invention.

Scatter rejection may further be enhanced by using a stationary or reciprocating grid 82, e.g., disposed below the upper surface of the detector housing or on the upper surface 80 of the active detector area. A variety of different grid configurations may be utilized in this regard. FIG. 8 illustrates one such grid configuration where the grid 82' is composed of transverse slats 84, for example, aligned with the detector and scan axes. Such a grid is analogous to a Bucky grid used in full field imaging applications. However, the illustrated grid 82' is contoured to generally match the shape of the housing 30 (FIG. 7). In addition, the major axis of each of the slats 84 may be aligned with the beam axis 75 (FIG. 5). In the context of the illustrated slot-scanner, the slots may therefore have an orientation that is dependent on their location relative to the scan axis and/or the detector axis. The various slats 84 function in a manner analogous to the collimator slats discussed above to block radiation not on the primary incidence pathway i.e., the beam axis 75.

Figure 9:
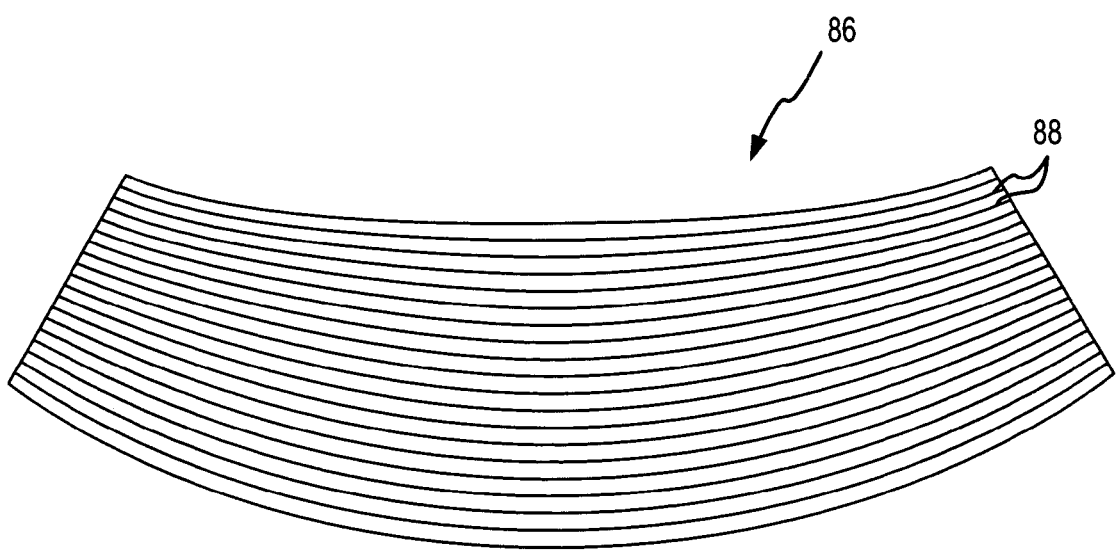

FIG. 9 shows an alternative grid configuration for slot-scanning applications. The illustrated grid 86 includes only slats 88 that are generally aligned with the scan axis. As noted above, collimator slats may be provided in connection with the detector, reducing or substantially eliminating the need for slats aligned with the detector axis. Thus, the grid design of FIG. 9 reduces grid line and dosage issues in relation to the design of FIG. 8. Nonetheless, such stationary or reciprocating grids result in grid lines in the image and/or require increased patient dosages. Moreover, such large grids may be difficult to reciprocate fast enough to provide the desired grid blurring at preferred scan rates/exposures.

Figure 10:
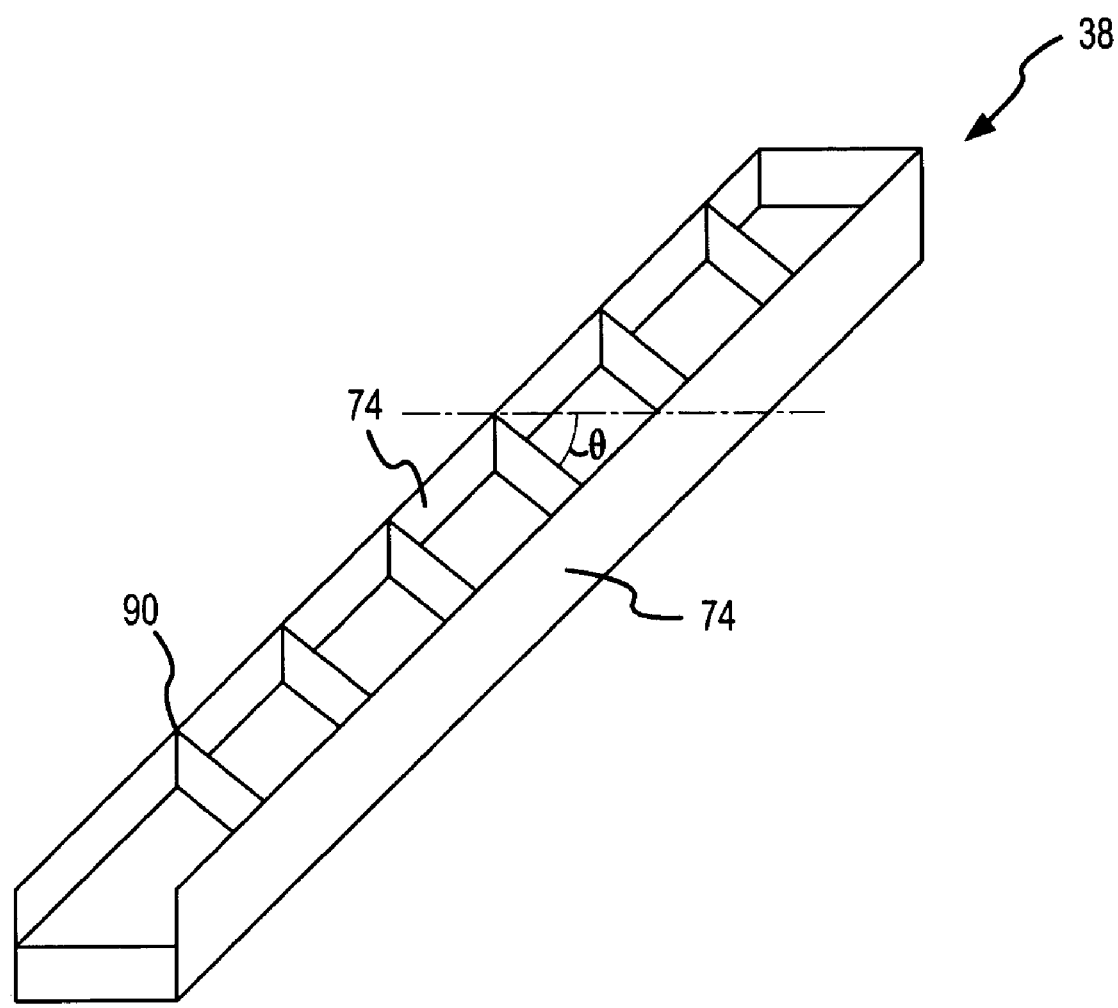

FIG. 10 shows a further alternative where slats 90 disposed at a non-zero angle, θ, with the scan axis are provided in connection with the active detector area 38. For example, the grid of FIG. 10 may be disposed on the detector assembly above the scintillator for movement with the detector assembly. The illustrated angling of the slats 90 blurs the slats 90 so that lines do not appear in the resulting image. Moreover, the blurring is accomplished via a unidirectional movement of the slats 90 together with the detector, as opposed to reciprocating Bucky-style movement, thereby eliminating the issues of source/grid drive synchronization, increased exposure period to allow sufficient blurring movement (though some dosage increase may be associated with grid shadowing of the primary signal), and potential grid drive malfunctions. It will be appreciated that the various slats of Figures above with a scan axis component are useful for blocking scatter traveling in or near to the plane of the detector axis and beam axis. Grid slat angles, height, width, parameters are optimized as a function of various system imaging parameters.

The present invention thus may include a number of components for reducing scatter generation and improving scatter rejection. Nonetheless, some amount of scatter may be detected. Accordingly, the present invention further reduces the effects of scatter through scatter compensation, e.g., post-detection processing to subtract scatter from the raw image data as discussed below.

3. Scatter Compensation

A. Gross Scatter Estimates and Spatially Dependent Estimates.

Scatter compensation relates to estimating the amount of detected scatter so that the image information from the detector can be adjusted to compensate for the effects of such scatter, e.g., via digital subtraction. This estimation may be based at least in part on scatter measurements or may be based on a mathematical model involving various scatter related parameters. With regard to scatter measurements, as noted above, the imaging system of the present invention may utilize an undercollimated beam. That is, the beam width may be less than the detector width. The extra "dark" detector area may be used to directly measure scatter in connection with certain detector read-out mechanisms. For example, a beam width of 8-mm and a detector width of 10-mm provides a 1-mm dark band at each detector edge which may be used for scatter detection, provided that these detector areas are separately read out or otherwise distinguished from the integrated charge associated with the primary signal. Such measurements may be interpolated to provide spatially indexed scatter data. Such an interpolation process may not be limited to linear interpolation but, rather, may take into account the spatial dependence (e.g., isotropic or forward peaked) characteristics of various scatter effects and grid performance.

With regard to mathematical modeling, substantial improvements in image quality can be achieved through gross scatter estimates independent of specific beam/scatter spatial distribution information. A further improvement can be achieved by modeling a scatter distribution based on reference measurements obtained during a calibration procedure or at some other test time. As discussed below, the present invention provides a still further improvement by taking certain measurements concurrent with image acquisition so that scatter compensation can be determined or scaled based on actual imaging conditions. The associated compensation models may be empirically and/or mathematically derived. A model is discussed below for addressing Rayleigh as well as Compton effects and single as well as multiple scatters.

It is clear that multiple scatters do not carry much information with respect to the origin of the first scattering event, and accordingly the multiple scatter distribution will be fairly uniform, slow-varying in space, and could be corrected by subtracting a simple constant or slowly varying function from the detected intensity distribution as discussed below (as, for example, a single constant or linear model for each line (row) in the image, plus smoothness constraints). On the other hand, single scatters will carry some geometric information. Indeed, the probabilistic properties of the Compton scatter distribution are accurately known (for a given scattering material). That is, as a function of incoming x-ray energy, the differential tissue cross sections allow analytic descriptions of the angular and energetic distribution of the scattered x-rays. (The analytic function is given by the Klein-Nishina expression). The Rayleigh scattering distribution is known experimentally for most materials of interest to within less than 10% error. Both of these functions have been included in various software Monte-Carlo codes that allow simulation of the scatter distribution to a very precise degree. Examples include the EGS4 code from Standford (Electron Gamma Showers, version 4, Standford Linear Accelerator Program), and TART2000.

It is clear from the above consideration that it is straightforward to carry out analytically calculations of the scatter-to-primary ratio (S/P) for sheets of uniform materials. These calculations can then be generalized to non-uniform materials, and from the estimates of scatter derived from the line-integrals of the x-ray attenuation coefficients, a correction method can be derived. These estimates can be checked, and the model parameters adjusted for optimal results, in the following two complementary ways. First, experiments can be carried out on the imaging system 10 (FIG. 1) with sheets of uniform density. By varying the distance from the sheets to the detector, an accurate approximation to the solid angle function and average depth of origin of scatters within the sheets may be determined. Accordingly, a simple correction model may be derived, and the parameters of this model may be further adjusted by carrying out Monte-Carlo experiments. These two complementary approaches will lead to a scatter-correction method that will allow subtraction of at least 70% of the scatter in the digital images of system 10.

The calculation of the line-integral through the object being imaged is a key component for an accurate estimate of scatter. This calculation in turn depends on taking the log of the ratio of detected intensity to impinging (or illuminating) intensity. Both of these quantities are measured in the system 10, and these measurement may be further refined. Indeed, the beam profile may be measured during a daily-calibration using the read out of a detector during a calibration scan or scans. This impinging beam can be further observed by introducing at the beginning (and/or end) of the scan an attenuator, for example, an acrylic wedge of known geometry and properties as described above, such that under all expected imaging techniques, a non-saturated vector of data can be acquired representing the anterior-posterior beam intensity profile. Another attenuator, e.g., an acrylic wedge, located at the anterior edge of the field-of-view, and parallel to the scan axis, can be used in similar fashion to track the intensity variations during the scan. Such wedges 92 are shown in FIGS. 3A-3C and FIG. 11A.

Figure 11C:
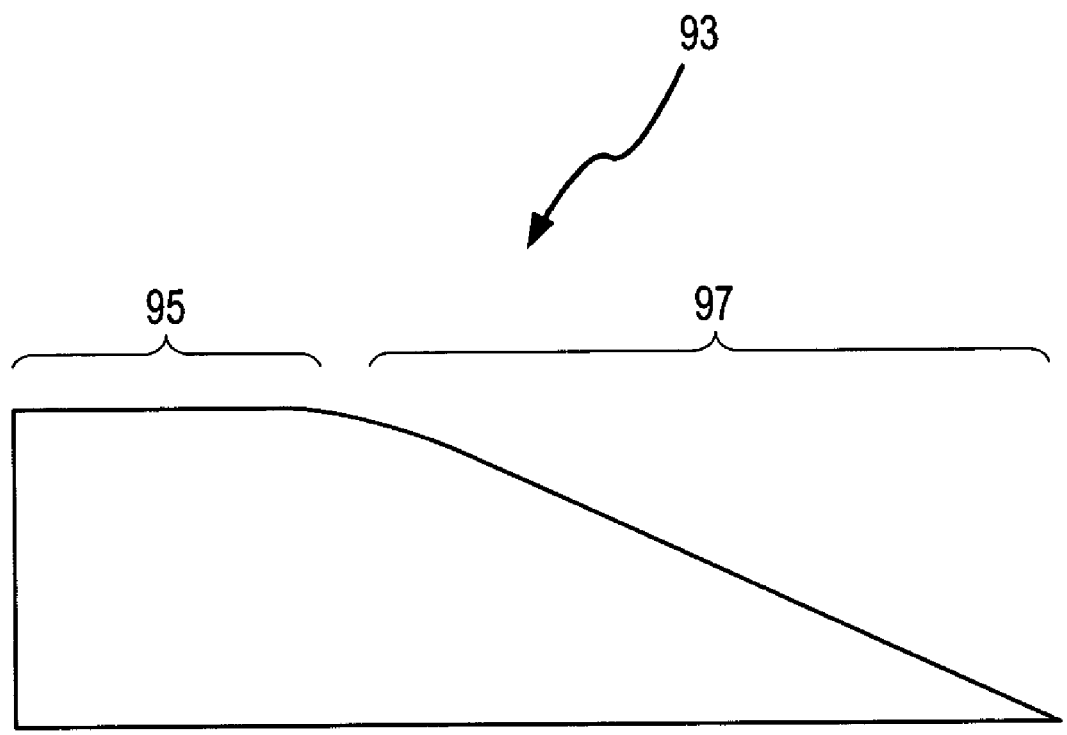
FIG. 11C is a side view showing an alternative attenuator configuration in accordance with the present invention.

FIG. 11C shows an alternative wedge profile that may be utilized for one or more of the elements 76 and 92. As shown, the wedge 93 includes an initial rectangular cross-section portion 95 and a tapered portion 97. In this manner, substantially constant attenuation characteristics are provided over the rectangular portion 95 and associated detector elements can be readily integrated or read out to provide averaged or composite information.

The information associated with the wedges 92 together with the output associated with anterior attenuator 76 allows for precise determination of the impinging illumination profile over the scan area. This information, in conjunction with the recorded digital data, allows direct log calculation (according to Beer's law) and determination of the line-integrals The x-ray variations introduced by the attenuators 76 and 92 themselves can be easily characterized (e.g., empirically) and subtracted from the digital image. Similarly, the high-resolution collimator blades (located at the x-ray source collimator) could be designed to include a semi-opaque material that would serve the same purpose for high-resolution imaging.

Further, direct experimentation with blocks of uniform sheets, at any kVp, but with low mA to allow collection of non-saturated data, will provide a further means of model development and improvement, by allowing comparison of x-ray profiles just outside a phantom, e.g., a standardized acrylic mass) with and without the uniform sheet material in the beam. Other means of estimating the scatter distribution include the use of beads and/or variable apertures (totally blocking the primary and therefore allowing an estimate of the scatter intensity distribution in the bead shadow). Such approaches are effective in modeling a low-frequency scatter function that can be scaled to reflect specific imaging techniques (kVp, mA), and material thicknesses (as measured by the system). Scatter correction then ensues by subtraction of the scaled low-frequency scatter distribution.

It is important to recognize that in slot-scanning technology, due to the potential absence of a grid, the scatter distribution may not have certain high-frequency components as observed with systems using a two-dimensional detector and scatter-rejection grid. This is because a scatter rejection grid is most effective at removing scatter originating at greater distance from the point under consideration in the image, as such scatter will impinge on the detector with a larger angle and therefore be more likely absorbed by the grid slats. Conversely, due to the preferential rejection of multiple and Compton scatters in a slot-scanning system, the scatter frequency components may contain more high-frequency components than what would be observed on a grid-less, 2D area detector. In summary, a significant part of the scatter in slot-scanning technology may be taken out with a relatively simple, low-frequency model. It should also be pointed out that part of that slowly-varying scatter distribution is removed by the image presentation algorithm conventionally executed as part of digital imaging processing, as this algorithm includes a type of unsharp masking, whereby the low-frequency components of the image are subtracted or much attenuated in the corrected image to improve high-frequency component contrast. It should also be recognized that use of time delay integration as described above (TDI), when scatter-only measurements are directly available, will provide further data regarding the spatial distribution of the scatter, and therefore can be leveraged to improve the efficacy of scatter-correction algorithms.

Further, the use of multi-views in mammography, tomosynthesis and three-dimensional imaging is useful in refining the scatter distribution estimate by allowing precise determination of the location of specific scatterers (such as dense masses, micro-calcifications, etc) in a 3-D volume. In the multi-view case, a 3-D reconstruction of the linear attenuation coefficient leads to very precise, iterative scatter correction, by allowing forward projection and calculation of the single (and by generalization, multiple of any given order) scatter distribution (and correction by subsequent subtraction). Concurrent ultrasound images may also be used in this regard for locating scatterers and characterizing tissue composition. In any case, a mathematical model for estimating scatter based on certain scatter related parameters may be developed for the imaging system as described below.

B. Basis for Scatter Model.

Considering the patient's breast under compression, optionally including the compression assembly, let $I_0$ denote the impinging x-ray intensity. Let P denote the exit intensity being detected (in the absence of scatter), and let S be the detected scatter intensity, considering one detector element during an integration time $\Delta t$, illuminated by a pencil beam of x-ray covering exactly the area A of the pixel under consideration.

The goal of a first calculation is to determine the amount of scatter intensity illuminating a point M'. At diagnostic x-ray energies, the total linear attenuation coefficient can be decomposed as follows:

$$\mu(l,E) = [\mu_{Compton}(l,E) + \mu_{Rayleigh}(l,E)] + \mu_{Photo-Electric}(l,E) \quad (1)$$

where the first term [in bracket] on the right-hand side of the equation is the total scatter component of the linear attenuation coefficient, sum of the Compton and Rayleigh components, while the last term on the right-hand side is the photoelectric component, corresponding to the probability of total attenuation of the x-ray. The linear attenuation coefficient and its components are seen to be dependent upon the coordinate l along the path length (line-integral) being considered.

Accordingly the detected primary is given by:

$$P = \int_{Spectrum} I_0(E) \exp\left\{-\int_{pathL} [\mu(l,E)] dl\right\} dE \quad (2)$$

and the total image signal recorded is given by the sum of the primary P and (total) scatter S components:

$$I = P + S \quad (2\text{-}b)$$

In projection imaging, 3-D information is not known (regarding the object composition) so that in a first approximation only the line-integral of the attenuation coefficient is measurable, as given by a simplification of equation (2) above:

$$P = I_0 \exp\left\{-\int_{pathL} [\mu(l, E_{Eff})] dl\right\},$$

Where $E_{eff}$ is the beam effective energy.

Knowing the total path-length L, as for example given by the compression thickness indicated by the system, one obtains the following estimate expression for the average linear attenuation coefficient at the effective beam energy:

$$\bar{\mu} = -\frac{1}{L} \text{Log} \frac{P}{I_0} \quad (3)$$

On a mammography system, the thickness indication L is estimated by a combination of distance measurement and applied compression force. Other means of estimating the compressed thickness are available, such as optical imaging, etc. Accordingly, a two-dimensional map of compressed breast thickness, L(x,y) may be obtained, and used on a point-by-point basis in equation (3) and elsewhere in the scatter correction model.

The attenuation coefficients are also known to be a function of the x-ray energy. Knowing the technique selected for a particular examination, such as retained kVp and mAs, and based upon a characterization of the x-ray tube spectrum, it is possible to model the beam spectral shape at any point along an attenuation path of known characteristics. In the absence of detailed knowledge about the 3-D structure of the object of interest, simple models provide approximate information that is sufficient for a first order estimation of the generated scatter.

A simple first order model follows. The tissues being imaged are assumed to be composed of water only. Based on the tabulated attenuation properties of water, it is then possible to estimate the effective energy Eeff such that:

$$\bar{\mu} = -\frac{1}{L} \text{Log} \frac{P}{I_0} \approx -\frac{1}{L} \text{Log} \frac{I}{I_0} = \mu_{water}(Eeff) \quad (4)$$

Note that due to the presence of detected scatter in the intensity measurement I (I=S+P), the resulting estimate $E_{eff}$ will be biased. The scatter correction process might therefore be made iterative, where a second, improved estimate of $E_{eff}$ ensues scatter correction as described below.

A higher order model may also be employed, whereby the linear attenuation coefficient is decomposed onto two basis vectors. Knowledge of the compressed thickness, emitted spectrum at selected kVp, and detector response as a function of energy enables finding the respective coefficients of the two basis functions. More generally, by decomposing the linear attenuation coefficient onto N (known) basis functions $\mu_i(E)$:

$$\mu(l, E) = \sum_{i=1}^{N} \alpha_i(l) \times \mu_i(E), \quad (5)$$

where the $\alpha_i(l)$ are the decomposition coefficients, dependent upon the distance l along the path from the x-ray source to the pixel being considered, one obtains by substituting in (2) above:

$$P = \int_{Spectrum} I_0(E) \times \exp\left[-\int_L \sum_{i=1}^{N} \alpha_i(l) \times \mu_i(E) dl\right] dE, \quad (6)$$

subject to (s.t.):

$$\sum_{i=1}^{i=N} \alpha_i(l) = 1. \quad (7)$$

By commuting the sum and integral signs in (6), and integrating both sides of (7) over the path L:

$$P = \int_{Spectrum} I_0(E) \times \exp\left[-\sum_{i=1}^{i=N} \mu_i(E) \int_L \alpha_i(l) dl\right] dE, \quad (8)$$

s.t.:

$$\int_L \sum_{i=1}^{i=N} \alpha_i(l) dl = L \quad (9)$$

wherein (9) L represents L(x,y) for the pixel under consideration.

Accordingly, by defining the N unknowns:

$$A_i = \int_L \alpha_i(l) dl, i = 1, \ldots, N,$$

The following two equations are obtained:

$$P = \int_{Spectrum} I_0(E) \times \exp\left[-\sum_{i=1}^{i=N} A_i \times \mu_i(E)\right] dE, s.t: \quad (10)$$

$$\sum_{i=1}^{N} A_i = L. \quad (11)$$

From linear system theory, it is well known that given M equations (forming a non-singular system), M unknown may be determined by system inversion. Accordingly the system of equations (10) and (11) supports the decomposition of the attenuation coefficients onto two basis functions. Examples in general radiography would include bone and soft-tissue; in mammography, these two basis functions may be chosen as water and calcium, or as fibroglandular (dense) and adipose (fat) tissues.

Further, it is clear that addition of one or more measurements, such as obtained by changing the beam kVp, would lead to the following system of M+1 equations:

$$P_i = \int_{Spectrum_j} I_0(E) \times \exp\left[-\sum_{i=1}^{i=N} A_i \times \mu_i(E)\right] dE, \quad (12)$$

$$j = 1, \ldots M, s.t:$$

$$\sum_{i=1}^{N} A_i = L. \quad (13)$$

Accordingly, and for illustration in the context of mammography, with measurements of the line-integral attenuation at M=2 different spectra (obtained for example either by changing the beam kVp and/or changing the beam filtration), it is possible to decompose the tissues onto three basis functions, such as fibroglandular tissue, adipose tissue, and calcium. Other basis functions choice are possible, and can be tailored to the specific application.

In the following, a model is proposed for the estimation of detected scatter, by decomposing scatters into single scatters and multiple scatters.

C. Single Scatter Estimation.

The following analysis is conducted for the Compton components. The Rayleigh estimate would be obtained by substituting all quantities (such as differential scatter cross-sections) for Compton with the corresponding quantity for Rayleigh.

The collision cross-section $\sigma^C$ determines the probability that an incident photon will undergo a Compton scatter. In a thin layer of thickness dx, the probability of scattering is given by the fraction of the beam that is occluded by the scattering sites:

$$\text{Proba\_of\_scatter} = -\frac{d\phi}{\phi} = n_e \times \sigma^C \times dx, \quad (14)$$

where $\Phi$ is the photon fluence in photons per square centimeters, $n_e$ is the electron density (cm$^{-3}$), $\sigma^C$ is the Compton collision cross-section (cm$^2 \times$g$^{-1}$), and $\mu^C$ is the Compton linear attenuation coefficient. The electron density $n_e$ is given by:

$$n_e = N_0 \times \rho \times \frac{Z}{A}, \quad (15)$$

$N_0$ Avogadro's number
$\rho$: material density
A: atomic weight;
Z: atomic number The number of photons scattered per unit volume is then given by:

$$\frac{dN_s}{dV} = -\frac{d\phi}{dx} = \phi \times n_e \times \sigma^C \quad (16)$$

The differential cross-section $$\left(\frac{d\sigma^C}{d\Omega}\right)_\Psi$$

is defined such that $d\sigma^C$ is the probability that an incident photon will be deflected into the elemental solid angle $d\Omega$ when passing through an attenuator containing one scattering per unit area, at angle $\psi$. Accordingly:

$$\sigma^C = 2\pi \int_0^\pi \left(\frac{d\sigma^C}{d\Omega}\right)_\Psi \sin\Psi d\Psi, \quad (17)$$

or differentiating (16) with respect to $\Omega$:

$$\left[\frac{d^2 N_s}{dV d\Omega}\right] = \phi \times n_e \times \left(\frac{d\sigma^C}{d\Omega}\right)_\Psi. \quad (18)$$

The amount of energy $d^2E_s$ that is scattered into an elementary solid angle $d\Omega$ from the elemental volume dV is:

$$\left[\frac{d^2 E_s}{dV d\Omega}\right]_\Psi = \quad (19)$$
$$hv' \times \phi \times n_e \times \left(\frac{d\sigma^C}{d\Omega}\right)_\Psi = hv_0 \times \left(\frac{hv'}{hv_0}\right) \times \phi \times n_e \times \left(\frac{d\sigma^C}{d\Omega}\right)_\Psi.$$

Accordingly, the amount of energy scattered by the object being imaged into an annulus of radius dr located at distance r from M is given by:

$$S_C = \int_{l=0}^{l=L} \left\{ I'(l) \exp\left[-\overline{\mu}\frac{(L-1)}{\cos\Psi}\right] \left(\frac{d^2 E}{dV d\Omega}\right) d\Omega \right\} dV(l) \quad (20)$$

with:

$$dV(l) = A \times dl.$$

where I'(l) represents the illuminating intensity at position l along the line-integral, the term within the exponential is the attenuation from the elemental volume dV at position l along the line-integral to point M', and the last term inside the curly brackets represents the amount of energy scattered into an elementary solid angle $d\Omega$ from the elemental volume dV as calculated above.

The solid angle $d\Omega$ is simply given by:

$$\frac{dA}{R^2},$$

where $dA=2\pi \times r \times dr$ and $R^2=[L-l]^2+r^2$. Also, $I'=I_0 \times \exp(-\bar{\mu} \times l)$, so that by substituting one obtains:

$$s = \int_{l=0}^{l=L} \left\{ I_0 \exp(-\bar{\mu} \times l) \exp\left[-\bar{\mu} \frac{(L-l)}{\cos\Psi}\right] \times n_e \times h v_0 \times \left[\left(\frac{hv'}{hv}\right)(\Psi) \times \left(\frac{d\sigma^C}{d\Omega}\right)_\Psi \right] \left(\frac{2\pi \times r \times dr \times \cos(\Psi)}{[L-l]^2 + r^2}\right) \right\} dV(l) \quad (21)$$

where the term in the second square bracket inside the integral is the well-known Klein-Nishina function, that lists the differential cross-sections as a function of incoming energy $hv_0$ and scatter angle $\psi$. The Klein-Nishina formula also gives the scattered photon energy, $hv'$, as a function of the incoming photon $hv_0$ and scattering angle $\psi$. The total scatter radiation detected at a point M' is then obtained by first calculating the relative contribution of the corresponding annulus to pixel M', and then integrating the result over all image rays. It is clear to those skilled in the art that several computation arrangements and simplifications are possible to effectively carry out the calculations.

D. Multiple Scatters Estimation.

It is clear that the larger the amount of attenuation, the larger the amount of radiation scattered. However, due to self-attenuation, the amount of detected single scatters does not necessarily increase simply as a function of object size. The total amount of scatter generated within the object increases with object size. A model that has been shown to work well in estimating the multiple scatter (as determined by Monte-Carlo calculations and verified by experimentation) is:

$$\text{Multiple} \propto [\alpha + \beta \times S_C + \gamma \times S_R] \times \left[ \left( \varepsilon + \delta \times \int_L \mu(l) dl \right) \right],$$

where $\alpha$, $\beta$, $\gamma$, $\epsilon$, and $\delta$ are constants, and the term in square brackets represent a weighted average of the line-integrals calculated over a neighborhood of the pixel under consideration, and $S_C$, $S_R$ are the Compton and Rayleigh single scatter estimates respectively.

In practice, the multiple scatter component tends to vary fairly slowly spatially, and the constants may be determined semi-empirically from laboratory experiments and/or Monte-Carlo simulations.

The total scatter estimate is given simply as the sum of the single scatter components, Compton and Raleigh, added to the estimate of multiple scatters. It is apparent that this model may utilize various scatter parameters including geometric parameters, such as the air gap distance and patient thickness and composition, and imaging parameters such as the spatial intensity profile of the beam. In one implementation of the system as shown in FIG. 7, at least some of these parameters are determined automatically at imaging time with the patient positioned for an imaging procedure and are recorded in memory 92 accessible via a processor 90 for performing scatter-related computations.

Specifically, outputs from the drive motor 80 and a resistance sensor 94 may be used to determine the compression force or pressure applied to the patient or a profile of resistance as a function of progressive compression. For example, the sensor 94 may include a strain gauge, pressure transducer or the like. The drive motor 80 and/or position sensor 96 may provide an indication of the position of the paddle 52. This in combination with similar outputs from a motor or position sensor 98 associated with the support plate 78 can be used to determine the tissue thickness. The tissue thickness distribution as a function of pixel coordinates (x,y) may be estimated from applied compression force, paddle deflection model, optical or other means. Also, as discussed above, readings related to the various attenuators can be used to provide a spatial intensity profile for the image area.

The structure of FIG. 7, including patient support/compression elements 52 and 78 that may be made independent of the motion of the source/detector gantry, has advantages for various applications such as three-dimensional imaging. For example, this structure allows for maintaining the patient in a fixed (compressed) position while rotating the gantry to acquire images from different projection orientations that can be processed to generate spatial images and to spatially localize areas of interest, e.g., for minimally invasive sampling or treatment, or to guide surgeons.

Figure 12:
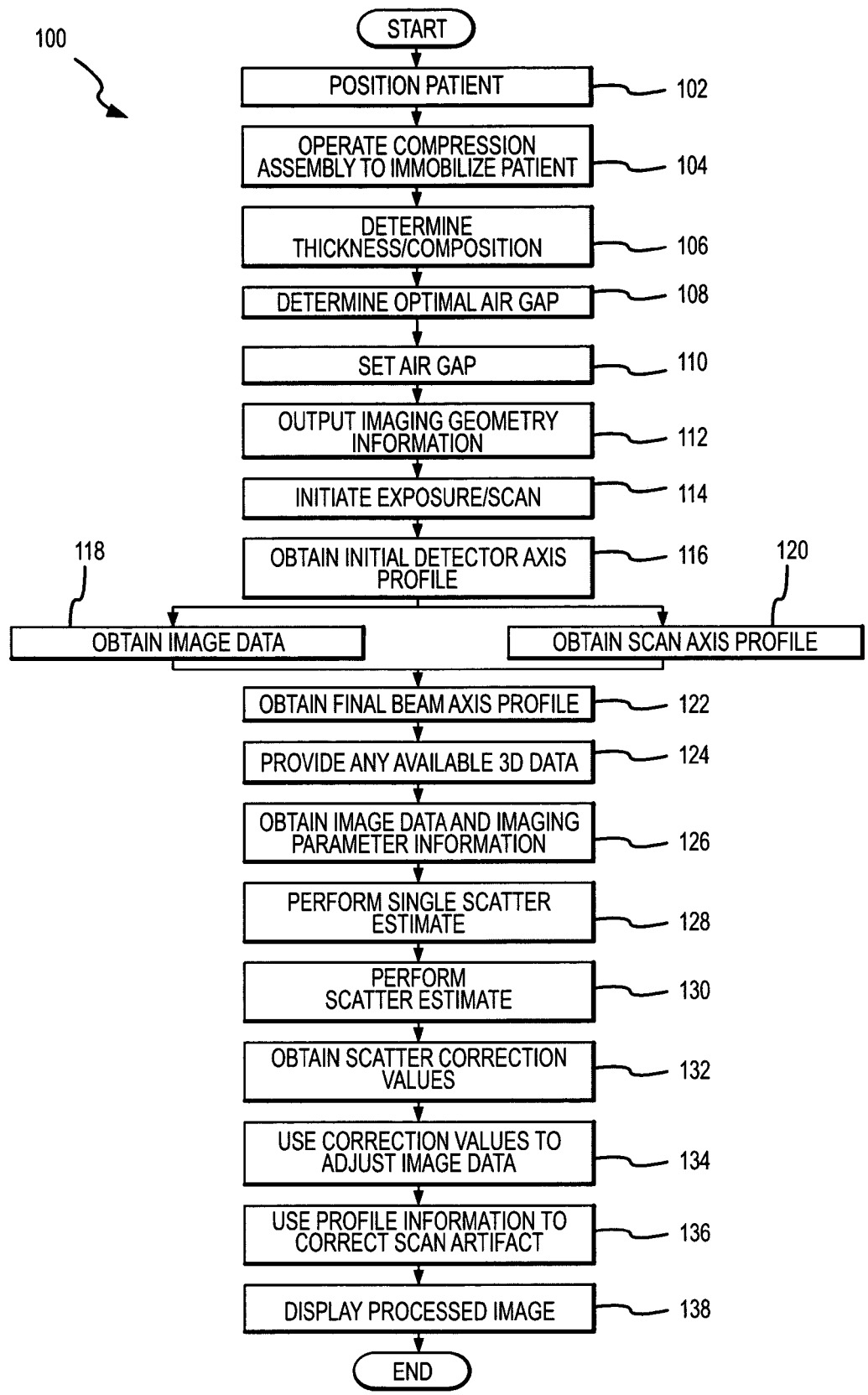
FIG. 12 is a flow chart illustrating a process for reducing the effects of scatter in accordance with the present invention.

An overall process 100 for reducing the effects of scatter in accordance with the present invention is illustrated by the flow chart of FIG. 12. The process is initiated by positioning (102) the patient for a mammographic procedure. This may involve positioning the patient's breast on a support plate in a desired position between the x-ray imaging source and the detector. A compression assembly may then be operated (104) to compress the patient's breast. For example, a compression paddle on the side of the patient's breast opposite the support plate may be lowered to provide the desired compression. This action may be manual or automatic. In the case of an automatic compression assembly, this may involve activating the drive motor to apply a desired compression pressure or force.

To improve scatter compensation, the thickness and/or composition of the patient's breast may be determined (106). The thickness may be determined and entered into the processor automatically or manually. In the case of manual determination, a scale provided in connection with the movable compression paddle may be used to determine the compressed thickness. In the case of an automatic compression assembly, an output from the compression motor or an encoder may be used to record the compressed thickness. Similarly, the composition may be determined manually or automatically. In this regard, an experienced physician may evaluate the tissue compensation and make an appropriate entry via a user interface. Alternatively, a resistance sensor associated with the movable compression paddle may be used to provide a measure of the compression force applied or a profile of the resistance encountered during progressive compression of the patient's breast so as to provide an indication of tissue composition. Alternatively or in complement, previous film and/or digital image of the patients may be processed automatically to provide an estimate of tissue density, thereby allowing one additional term in the basis function decomposition (12). The thickness and composition information is stored in memory for use by the processor in scatter compensation calculations.

The processor may then be operated to determine (108) an optimal air gap between the patient's breast and the detector surface. As noted above, such optimization may be based on the at least the thickness of the patient's compressed breast. Once this optimal air gap is determined, the actual air gap of the system may be set (110) to minimize scattered detection. This may involve repositioning the detector housing and/or the support plate, and/or the detector within the housing, and may be carried out with simultaneous gantry elevation compensation so that the patient position remains unchanged during the process.

As noted above, various imaging geometry information may be output (112) to memory associated with the processor prior to, during or after an image exposure. In any event, an imaging exposure and scan is initiated (114) by activating the source and operating the scan motor to drive the detector and source through a scan motion. At the beginning of the scan motion, an initial beam axis profile relative to the detector axis may be obtained (116) by scanning across a detector access attenuator and reading out the corresponding detector elements. During the scan, a scan axis profile may be obtained (120) by reading out the detector elements associated with a scan axis attenuator. Concurrent with obtaining the scan axis profile in the illustrated process, the image data is obtained (118) by reading out the detector elements associated with the image area. Finally, a final beam or detector axis profile may be obtained (122) by reading out the detector elements associated with another detector axis attenuator disposed at the end of the scan. These various profile measurements may be utilized to develop an overall beam intensity profile. For example, the detector axis profile for a given point in the scan may be determined by interpolating between the scan start and scan end profiles as measured using the detector axis attenuators. This profile may then be scaled using the output from the scan axis attenuator such that profile information can be obtained for each desired area or each point or pixel of the detector array over the course of a scan. Any available three-dimensional information, e.g., based on stereo imaging or ultrasound measurements, may also be provided (124) to the processor at an appropriate time. The associated image data and imaging parameter information is output (126) to the memory associated with the processor for use in scatter compensation calculations.

The mathematical model discussed above is then used to perform (128) a single scatter estimate and perform (130) a multiple scatter estimate. These calculations may use the various outputs discussed above including beam intensity profile information, patient thickness and composition information and other geometric parameters such as air gap distance. The single scatter estimate and a multiple scatter estimate are combined to determine a total scatter estimate which, in turn, is used to obtain (132) scatter correction values on a pixel-by-pixel basis. The raw imaging information is then corrected (134) using these values. For example, this correction may be implemented by a digital subtraction process. Profile information may also be used to correct (136) for any scan artifact, e.g., due to scan motion transients. The corrected or adjusted imaging data may then be displayed (138) on a monitor. The result is that the effects of scatter are substantially reduced allowing for improved contrast, improved resolution, reduced patient dosages and improved diagnosis.

Those skilled in the art will now see that certain modifications can be made to the assembly and methods herein disclosed with respect to the illustrated embodiments, without departing from the spirit of the present invention. And while the invention has been described above with respect to the preferred embodiments, it will be understood that the invention is adaptable to numerous rearrangements, modifications, and alterations, and all such arrangements, modifications, and alterations are intended to be within the scope of the appended claims.

What is claimed:

1. A method of imaging a selected tissue region of a patient's body, comprising the steps of: transmitting radiation into said selected tissue region of said patient's body during an exposure period; detecting radiation from said selected tissue region of said patient's body, wherein detected radiation from said selected tissue region includes a scattered portion corresponding with photonic energy scattered within said selected tissue region, and a non-scattered portion corresponding with photonic energy passing through said selected tissue region substantially free from scattering; estimating first and second parts of said scattered portion, wherein said first part corresponds with photonic energy passing through said selected tissue region with a single scattering occurrence, and wherein said second part corresponds with photonic energy passing through said selected tissue region with multiple scattering occurrences; obtaining radiographic image data in relation to said detected radiation from said selected tissue region; and, utilizing the estimated first and second parts of said scattered portion to adjust said radiographic image data.

2. A method as recited in claim 1, wherein said first part includes at least one of a Compton scatter component and a Rayleigh scatter component.

3. A method as recited in claim 2, wherein said estimating step includes: determining said at least one of a Compton scatter component and a Rayleigh scatter component as a function of a measured dimension of said selected tissue region.

4. A method as recited in claim 3, wherein said estimating step further includes: determining each of a Compton scatter component and a Rayleigh scatter component as a function of said measured dimension of said selected tissue region.

5. A method as recited in claim 3, wherein said estimating step further includes: determining said second part of said scattered portion as a function of said measured dimension of said selected tissue region.

6. A method as recited in claim 3, further comprising: locating said selected tissue region at a substantially fixed location; measuring a thickness of said selected tissue region, wherein said thickness is employed as said measured dimension in said determining step; and, completing said transmitting, measuring and obtaining steps during said locating step.

7. A method as recited in claim 6, wherein said locating step includes: compressing said selected tissue region with a known compression force; and, wherein said estimating step further includes: determining said at least one of a Compton scatter component and a Rayleigh scatter component as a function of said thickness of and said compression force applied to said selected tissue region.

8. A method as recited in claim 3, wherein said estimating step further includes: determining said at least one of a Compton scatter component and a Rayleigh scatter component as a function of said measured dimension and an estimated density of at least a portion of said selected tissue region.

9. A method as recited in claim 8, wherein said estimating step further includes: determining each of a Compton scatter component and a Rayleigh scatter component as a function of said measured dimension and said estimated density of said selected tissue region.

10. A method as recited in claim 8, further comprising: selecting said estimated density from a plurality of estimated densities that correspond with a plurality of predetermined tissue types.

11. A method as recited in claim 8, wherein said estimating step further includes: determining said at least one of a Compton scatter component and a Rayleigh scatter component as a function of said measured dimension, said estimated density and an estimated intensity value of said transmitted radiation incident upon said selected tissue region.

12. A method as recited in claim 11, further comprising: setting a power level for said radiation transmission; and, establishing said estimated intensity value as a function of said power level.

13. A method as recited in claim 12, further comprising: locating said selected tissue region at a substantially fixed location; measuring an intensity value of said transmitted radiation; completing said transmitting, obtaining and measuring steps during said locating step; and, adjusting said estimated intensity value utilizing said measured intensity value, wherein an adjusted intensity value is obtained for use in said estimating step.

14. A method as recited in claim 1, wherein said estimating step includes: determining at least one of a Compton scatter component and a Rayleigh scatter component as a function of an intensity value of said transmitted radiation incident upon said selected tissue region.

15. A method as recited in claim 14, wherein said intensity value is an estimated intensity value, and further comprising: setting a power level for said radiation transmissions; and, establishing said estimated intensity value as a function of said power level.

16. A method as recited in claim 15, further comprising: locating said selected tissue region at a substantially fixed location; measuring an intensity of said detected radiation; completing said transmitting, obtaining and measuring steps during said locating step; and, adjusting said estimated intensity value utilizing said measured intensity, wherein an adjusted intensity value is used in said determining step.

17. A method as recited in claim 16, wherein said substantially fixed location corresponds to a predetermined imaging frame of reference, wherein said predetermined imaging frame of reference comprises a plurality of areas, and wherein said obtaining, estimating and utilizing steps are completed in separate, corresponding relation to each of said plurality of areas.

18. A method as recited in claim 17, wherein said plurality of areas define a matrix having at least a first dimension, and wherein said establishing and measuring steps are completed in separate, corresponding relation to each of said plurality of areas as a function of location in said at least first dimension.

19. A method as recited in claim 17, wherein said matrix has a second dimension, and wherein said establishing and measuring steps are completed in separate corresponding relation to each of said plurality of areas as a function of location in each of said first and second dimensions.

20. A method as recited in claim 19, wherein said measuring step includes: detecting a plurality of intensities of said transmitted radiation utilizing first and second arrays of pixel elements extending in said first and second dimensions, respectively, and located outside of said predetermined imaging frame of reference.

21. A method as recited in claim 17, wherein said plurality of areas define a matrix having first and second dimensions, and wherein said obtaining step includes: detecting said transmitted radiation passing through said selected tissue region utilizing an active array of pixel elements extending entirely across said predetermined imaging frame of reference in said second dimension and partially across said predetermined imaging frame of reference in said first dimension.

22. A method as recited in claim 21, wherein said detecting step includes: moving said active array of pixel elements across said predetermined imaging frame of reference.

23. A method as recited in claim 22, wherein said transmitting step includes: scanning a radiation beam across said predetermined frame of reference synchronous with said movement of the array.

24. A method as recited in claim 22, further comprising: optically blocking some of said second part of said scattered portion from reaching said array of pixel elements.

25. A method as recited in claim 1, wherein said utilizing step includes: subtracting said first and second parts from said radiographic image data to adjust the image data; and, displaying the adjusted radiographic image data.

26. A method as recited in claim 1, further comprising obtaining a first value related to a first tissue composition corresponding to a first portion of said selected tissue region and a second value related to a second tissue composition corresponding to a second portion of said selected tissue region and using said first and second values to estimate one of said first and second parts of said scattered portion.

27. An apparatus for use in imaging a selected tissue region of a patient's body, comprising: a source for transmitting radiation into said selected region of said patient's body; a detector for detecting radiation from said selected region of said patient's body, wherein detected radiation from said selected tissue region includes a scattered portion corresponding with photonic energy scattered within said selected tissue region, and a non-scattered portion corresponding with photonic energy passing through said selected tissue region substantially free from scattering; and a processor operative for: estimating first and second parts of said scattered portion, wherein said first part corresponds with photonic energy passing through said selected tissue region with a single scattering occurrence, and wherein said second part corresponds with photonic energy passing through said selected tissue region with multiple scattering occurrences; obtaining radiographic image data in relation to said detected radiation from said selected tissue region; and, utilizing the estimated first and second parts of said scattered portion to adjust said radiographic image data.

28. An apparatus as set forth in claim 27, wherein said source is operative for transmitting said radiation in a form of a beam having a first beam dimension that is less than a corresponding dimension of said selected region of said patient's body.

29. An apparatus as set forth in claim 28, wherein said source is operative for scanning said beam across said area of interest.

30. An apparatus as set forth in claim 27, wherein said detector includes and active detector area having a first detector dimension less than a corresponding dimension of said patient's body.

31. An apparatus as set forth in claim 27, wherein said processor is operative for receiving scatter related parameter information for a specific imaging procedure and using said parameter information to estimate one of said first and second parts.

32. An apparatus as set forth in claim 31, wherein said processor is operative for using said parameter information to estimate both of said first and second parts.

33. An apparatus as set forth in claim 31, wherein said parameter information relates to an intensity of radiation transmitted by said source.

34. An apparatus as set forth in claim 31, wherein said parameter information relates to a density of at least a portion of said selected tissue region of said patient's body.

35. An apparatus as set forth in claim 27, wherein said processor is operative for receiving measurement information, obtained with said patient disposed in an imaging position relative to said source and said detector, and using said measurement information to estimate one of said first and second parts.

36. An apparatus as set forth in claim 35, wherein said processor is operative for using said measurement information to estimate both of said first and second parts.

37. An apparatus as set forth in claim 35, wherein said measurement information relates to a dimension of said selected tissue region of said patient's body.

38. An apparatus as set forth in claim 35, wherein said measurement information relates to a compression force exerted on said selected tissue region of said patient's body.

39. An apparatus as set forth in claim 35, wherein said measurement information relates to an intensity of radiation incident on a detector area outside of a predetermined imaging frame of reference corresponding to said selected tissue region.

40. An apparatus as set forth in claim 35, wherein said measurement information relates to intensities of radiation incident on multiple detector areas outside of a tissue imaging portion of said detector.

41. An apparatus as set forth in claim 35, wherein said measurement information relates to a profile, relative to a first axis of said detector, of radiation intensities incident on said detector.

42. An apparatus as set forth in claim 41, wherein said measurement information relates to a profile, relative to a second axis different than said first axis, of radiation intensities incident on said detector.

43. An apparatus as set forth in claim 35, wherein said measurement information relates to a spacing between said selected tissue region and said detector.

44. An apparatus as set forth in claim 35, further comprising a user interface for entering said measurement information.

45. An apparatus as set forth in claim 35, further comprising a measurement device for use in automatically obtaining said measurement information.

46. An apparatus as set forth in claim 45, wherein said measurement device provides information regarding a dimension of said selected region of said patient's body.

47. An apparatus as set forth in claim 45, wherein said measurement device provides information regarding a compression force applied to said selected region of said patient's body.

48. An apparatus as set forth in claim 45, wherein said measurement device comprises a portion of said detector.

49. An apparatus as set forth in claim 27, further comprising an attenuator having known radiation attenuation characteristics for attenuating, on a spatially dependent basis, radiation directed to said detector wherein said attenuator is positioned relative to said detector outside of a predetermined frame of reference corresponding to said selected tissue region.

50. An apparatus as set forth in claim 27, wherein said processor is operative for determining a spacing between said selected tissue region and said detector so as to reduce one of said first and second parts of said scatter portion.

51. An apparatus as set forth in claim 50, further comprising a positioning mechanism for use in establishing said spacing between said selected tissue region and said detector.

52. An apparatus as set forth in claim 51, wherein said positioning mechanism is operative for establishing said spacing free from movement of said selected tissue region.

53. An apparatus as set forth in claim 27, further comprising a measurement device for measuring scattered radiation during said transmitting step.

54. An apparatus as set forth in claim 53, wherein said source transmits a beam of radiation and said measurement device comprises a portion of said detector outside of an area of a predetermined frame of reference corresponding to said selected tissue region.

55. A method of imaging a selected tissue region of a patient's body, comprising the steps of: transmitting radiation into said selected tissue region of said patient's body during an exposure period; detecting radiation from said selected tissue region of said patient's body, wherein detected radiation from said selected tissue region includes a scattered portion corresponding with photonic energy scattered within said selected tissue region, and a non-scattered portion corresponding with photonic energy passing through said selected tissue region substantially free from scattering; positioning a patient in a desired position for a radiographic procedure; with said patient positioned in said desired position, operating a parameter measurement device to measure a procedure specific value of a scatter related parameter and provide an output indicative thereof; obtaining radiographic image data in relation to said detected radiation from said selected tissue region; and operating a processor to receive said output and use said image-specific value of said scatter related parameter to adjust said radiographic image data, wherein said step of operating a processor comprises estimating first and second parts of said scatter portion, wherein said first part corresponds with photonic energy passing through said selected tissue region with a single scattering occurrence, and wherein said second part corresponds with photonic energy passing through said selected tissue region with multiple scattering occurrences.

56. A method as set forth in claim 55, wherein said first part includes at least one of a Compton scatter component and a Rayleigh scatter component.

57. A method of imaging a selected tissue region of a patient's body, comprising the steps of: transmitting radiation into said selected tissue region of said patient's body during an exposure period; detecting radiation from said selected tissue region of said patient's body; wherein detected radiation from said selected tissue region includes a scattered portion corresponding with photonic energy scattered within said selected tissue region, and a non-scattered portion corresponding with photonic energy passing through said selected tissue region substantially free from scattering; positioning a patient in a desired position for a radiographic procedure; with said patient positioned in said desired position, operating a parameter measurement device to measure a procedure specific value of a scatter related parameter and provide an output indicative thereof, obtaining radiographic image data in relation to said detected radiation from said selected tissue region; and operating a processor to receive said output and use said image-specific value of said scatter related parameter to adjust said radiographic image data, wherein said step of operating said processor comprises determining at least one of a Compton scatter component and a Rayleigh scatter component as a function of a measured dimension of said selected tissue region, and wherein said step of operating further comprises estimating first and second parts of said scattered portion, wherein said first part corresponds with photonic energy passing through said selected tissue region with a single scattering occurrence, and wherein said second part corresponds with photonic energy passing through said selected tissue region with multiple scattering occurrences.

58. A method of imaging a selected tissue region of a patient's body, comprising the steps of: transmitting radiation into said selected tissue region of said patient's body during an exposure period; detecting radiation from said selected tissue region of said patient's body, wherein detected radiation from said selected tissue region includes a scattered portion corresponding with photonic energy scattered within said selected tissue region, and a non-scattered portion corresponding with photonic energy passing through said selected tissue region substantially free from scattering; positioning a patient in a desired position for a radiographic procedure; with said patient positioned in said desired position, operating a parameter measurement device to measure a procedure specific value of a scatter related parameter and provide an output indicative thereof; obtaining radiographic image data in relation to said detected radiation from said selected tissue region; and operating a processor to receive said output and use said image-specific value of said scatter related parameter to adjust said radiographic image data, wherein said step of operating said processor comprises determining at least one of a Compton scatter component and a Rayleigh scatter component as a function of an estimated density of at least a portion of said selected tissue region.

59. A method of imaging a selected tissue region of a patient's body, comprising the steps of: transmitting radiation into said selected tissue region of said patient's body during an exposure period; detecting radiation from said selected tissue region of said patient's body, wherein detected radiation from said selected tissue region includes a scattered portion corresponding with photonic energy scattered within said selected tissue region, and a non-scattered portion corresponding with photonic energy passing through said selected tissue region substantially free from scattering; positioning a patient in a desired position for a radiographic procedure; with said patient positioned in said desired position, operating a parameter measurement device to measure a procedure specific value of a scatter related parameter and provide an output indicative thereof; obtaining radiographic image data in relation to said detected radiation from said selected tissue region; and operating a processor to receive said output and use said image-specific value of said scatter related parameter to adjust said radiographic image data, wherein said step of operating said processor comprises determining one of a Compton scatter component and a Rayleigh scatter component as a function of a transmitted intensity of radiation incident on said selected tissue region, and wherein said step of operating further comprises estimating first and second parts of said scattered portion, wherein said first part corresponds with photonic energy passing through said selected tissue region with a single scattering occurrence, and wherein said second part corresponds with photonic energy passing through said selected tissue region with multiple scattering occurrences.

60. A method of imaging a selected tissue region of a patient's body, comprising the steps of: transmitting radiation into said selected tissue region of said patient's body during an exposure period; detecting radiation from said selected tissue region of said patient's body, wherein detected radiation from said selected tissue region includes a scattered portion corresponding with photonic energy scattered within said selected tissue region, and a non-scattered portion corresponding with photonic energy passing through said selected tissue region substantially free from scattering; positioning a patient in a desired position for a radiographic procedure; with said patient positioned in said desired position, operating a parameter measurement device to measure a procedure specific value of a scatter related parameter and provide an output indicative thereof; obtaining radiographic image data in relation to said detected radiation from said selected tissue region; and operating a processor to receive said output and use said image-specific value of said scatter related parameter to adjust said radiographic image data, wherein said step of operating said processor comprises determining one of a Compton scatter component and a Rayleigh scatter component based on a measured intensity of said detected radiation, and wherein said step of operating further comprises estimating first and second parts of said scattered portion, wherein said first part corresponds with photonic energy passing through said selected tissue region with a single scattering occurrence, and wherein said second part corresponds with photonic energy passing through said selected tissue region with multiple scattering occurrences.

61. A method of imaging a selected tissue region of a patient's body, comprising the steps of: transmitting radiation into said selected tissue region of said patient's body during an exposure period; detecting radiation from said selected tissue region of said patient's body, wherein detected radiation from said selected tissue region includes a scattered portion corresponding with photonic energy scattered within said selected tissue region, and a non-scattered portion corresponding with photonic energy passing through said selected tissue region substantially free from scattering; positioning a patient in a desired position for a radiographic procedure; with said patient positioned in said desired position, operating a parameter measurement device to measure a procedure specific value of a scatter related parameter and provide an output indicative thereof; obtaining radiographic image data in relation to said detected radiation from said selected tissue region; and operating a processor to receive said output and use said image-specific value of said scatter related parameter to adjust said radiographic image data, wherein said step of obtaining radiographic image data comprises operating a detector to detect said detected radiation and provide a detector output indicative thereof, wherein said detector output reflects imaging information for different portions of interest obtained at corresponding different times of said exposure period, and wherein said step of operating further comprises estimating first and second parts of said scattered portion, wherein said first part corresponds with photonic energy passing through said selected tissue region with a single scattering occurrence, and wherein said second part corresponds with photonic energy passing through said selected tissue region with multiple scattering occurrences.

62. An apparatus for use in imaging a selected tissue region of a patient's body, comprising: a source for transmitting radiation into said selected region of said patient's body; a detector for detecting radiation from said selected region of said patient's body and providing first imaging information based thereon; a patient support for supporting the patient such that said selected region is maintained in a desired imaging position for a radiographic procedure; a sensor for measuring a procedure specific value of a scatter related parameter with said patient positioned in said desired imaging position and providing a sensor output indicative thereof; and a processor for receiving said first imaging information and said sensor output, and providing second imaging information based thereon, wherein said processor estimates first and second parts of said scattered portion, wherein said first part corresponds with photonic energy passing through said selected tissue region with a single scattering occurrence, and wherein said second part corresponds with photonic energy passing through said selected tissue region with multiple scattering occurrences.

63. An apparatus as set forth in claim 62, wherein said source is operative for transmitting said radiation in a form of a beam having a first beam dimension that is less than a corresponding dimension of said selected region of said patient's body.

64. An apparatus as set forth in claim 62, wherein said detector includes an active detective area having a first detector dimension less than a corresponding dimension of said patient's body.

65. An apparatus as set forth in claim 62, wherein said selected region of said patient's body comprises at least a portion of a patient's breast and said patient support comprises a support for supporting said patient's breast.

66. An apparatus as set forth in claim 65, wherein said support plate is separated from said detector by a selected air gap distance.

67. An apparatus as set forth in claim 62, wherein said sensor is operative for providing information regarding a dimension of said selected region of said patient's body.

68. An apparatus as set forth in claim 62, wherein said sensor is operative for providing information regarding a tissue density of said selected region of said patient's body.

69. An apparatus as set forth in claim 62, wherein said sensor is operative for providing information regarding an intensity of radiation incident on said detector.

70. A method for use in imaging a selected tissue region of a patient's body, comprising the steps of: transmitting a photonic energy relative to said area of interest of said patient's body during an exposure period of a radiographic procedure; first operating a detector to detect portions of said photonic energy that have interacted with said area of interest of said patient's body and provide a detector output indicative thereof, wherein said detector output reflects imaging information for different portions of said area of interest obtained at corresponding different times of said exposure period; establishing scatter compensation information for said radiographic procedure; and second operating a processor to process said detector output, using said scatter compensation information to provide reduced scatter composite imaging information of said area of interest of said patient's body, wherein said processor is operated to estimate first and second parts of said scattered portion, wherein said first part corresponds with photonic energy passing through said selected tissue region with a single scattering occurrence, and wherein said second part corresponds with photonic energy passing through said selected tissue region with multiple scattering occurrences.

71. A method as set forth in claim 70, wherein said first part includes at least one of a Compton scatter component and a Rayleigh scatter-component.

72. A method as set forth in claim 70, wherein said step of second operating comprises determining at least one of a Compton scatter component and a Rayleigh scatter component as a function of a measured dimension of said area of interest.

73. A method as set forth in claim 70, wherein said step of second operating comprises determining at least one of a Compton scatter component and a Rayleigh scatter component as a function of an estimated density of at least a portion of said area of interest.

74. A method as set forth in claim 70, wherein said step of second operating comprises determining one of a Compton scatter component and a Rayleigh scatter component as a function of a transmitted intensity of radiation incident on said area of interest.

75. A method as set forth in claim 70, wherein said step of second operating comprises determining one of a Compton scatter component and a Rayleigh scatter component based on a measured intensity of said detected radiation.

76. A method as set forth in claim 70, wherein said step of second operating comprises determining one of a Compton scatter component and a Rayleigh scatter component as a function of a spacing between a detector surface and said area of interest.

77. An apparatus for use in imaging a selected tissue region of a patient's body, comprising: an imaging source for transmitting photonic energy relative to said area of interest of said patient's body during an exposure period of a radiographic procedure; a detector for detecting portions of said photonic that have interacted with said area of interest of said patient's body and providing a detector output indicative thereof, wherein said detector output includes imaging information for different portions of said area of interest obtained at corresponding different times of said exposure period; and a processor for accessing scatter compensation information for said radiographic procedure and processing said detector output using said scatter compensation information to provide reduced scatter composite imaging information of said area of interest of said patient's body, wherein said processor is operative for determining at least one of a Compton scatter component and a Rayleigh scatter component as a function of an estimated density of at least a portion of said area of interest.

78. An apparatus as set forth in claim 77, wherein said portions include a scattered portion and said processor is operative for estimating first and second parts of said scatter portion, wherein said first part corresponds with photonic energy passing through said selected tissue region with a single scattering occurrence, and wherein said second part corresponds with photonic energy passing through said selected tissue region with multiple scattering occurrences.

79. An apparatus as set forth in claim 78, wherein said first part includes at least one of a Compton scatter component and a Rayleigh scatter component.

80. An apparatus as set forth in claim 77, wherein said processor is operative for determining at least one of a Compton scatter component and a Rayleigh scatter component as a function of a measured dimension of said area of interest.

81. An apparatus as set forth in claim 77, wherein said processor is operative for determining one of a Compton scatter component and a Rayleigh scatter component as a function of a transmitted intensity of radiation incident on said area of interest.

82. An apparatus as set forth in claim 77, wherein said processor is operative for determining one of a Compton scatter component and a Rayleigh scatter component based on a measured intensity of said detected radiation.

83. An apparatus as set forth in claim 77, wherein said processor is operative for determining one of a Compton scatter component and a Rayleigh scatter component as a function of a spacing between a detector surface and said area of interest.

* * * * *